(12) United States Patent
Schneider et al.

(10) Patent No.: US 7,520,848 B2
(45) Date of Patent: Apr. 21, 2009

(54) ROBOTIC APPARATUS FOR TARGETING AND PRODUCING DEEP, FOCUSED TRANSCRANIAL MAGNETIC STIMULATION

(75) Inventors: M. Bret Schneider, Portola Valley, CA (US); David J. Mishelevich, Playa del Rey, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 739 days.

(21) Appl. No.: 10/821,807

(22) Filed: Apr. 9, 2004

(65) Prior Publication Data

US 2005/0228209 A1    Oct. 13, 2005

(51) Int. Cl.
 *A61N 1/00* (2006.01)
(52) U.S. Cl. ...................................................... 600/13
(58) Field of Classification Search ............... 600/9–15; 128/897, 898
See application file for complete search history.

(56) References Cited

U.S. PATENT DOCUMENTS

| | | | |
|---|---|---|---|
| 5,207,223 A | 5/1993 | Adler | |
| 5,427,097 A | 6/1995 | Depp | |
| 5,531,227 A | 7/1996 | Schneider | |
| 5,891,034 A | 4/1999 | Bucholz | |
| 6,132,361 A | 10/2000 | Epstein et al. | |
| 6,179,770 B1 | 1/2001 | Mould | |
| 6,179,771 B1 | 1/2001 | Mueller | |
| 6,198,958 B1 | 3/2001 | Ives et al. | |
| 6,236,875 B1 | 5/2001 | Bucholz et al. | |
| 6,351,573 B1 | 2/2002 | Schneider | |
| 6,425,852 B1 | 7/2002 | Epstein | |
| 6,461,289 B1 * | 10/2002 | Muntermann .................. 600/9 |
| 6,571,123 B2 | 5/2003 | Ives et al. | |
| 6,572,528 B2 | 6/2003 | Rohan et al. | |
| 6,849,040 B2 * | 2/2005 | Ruohonen et al. ............. 600/14 |
| 6,972,097 B2 | 12/2005 | Yoshida et al. | |
| 7,088,210 B2 | 8/2006 | Day et al. | |
| 2002/0007128 A1 * | 1/2002 | Ives et al. .................... 600/544 |
| 2002/0097125 A1 | 7/2002 | Davey | |
| 2003/0004392 A1 | 1/2003 | Tanner et al. | |
| 2003/0028072 A1 | 2/2003 | Fischell et al. | |
| 2003/0050527 A1 | 3/2003 | Fox et al. | |
| 2003/0204135 A1 | 10/2003 | Bystritsky | |

(Continued)

FOREIGN PATENT DOCUMENTS

EP    0709115 A1    5/1996

(Continued)

OTHER PUBLICATIONS

Mark S. George, "Stimulating the Brain", Scientific American, Sep. 2003, pp. 67-73.

(Continued)

*Primary Examiner*—Samuel G Gilbert
(74) *Attorney, Agent, or Firm*—Shay Glenn LLP

(57) ABSTRACT

Techniques for applying electromagnetic energy to deep, targeted areas without overwhelming other areas are provided. One or more coils are moved relative to a target area and magnetic fields are applied to the target from multiple coil locations. As a result, the aggregate electromagetic energy applied to the target over time is greater than surrounding areas. Additionally, a model for testing and treatment planning is provided.

25 Claims, 19 Drawing Sheets

U.S. PATENT DOCUMENTS

| | | |
|---|---|---|
| 2004/0010177 A1 | 1/2004 | Rohan et al. |
| 2004/0077921 A1 | 4/2004 | Becker et al. |
| 2004/0078056 A1 | 4/2004 | Zangen et al. |
| 2005/0113630 A1 | 5/2005 | Fox et al. |
| 2005/0148808 A1* | 7/2005 | Cameron et al. ............... 600/13 |
| 2005/0222625 A1 | 10/2005 | Laniado et al. |
| 2005/0228209 A1 | 10/2005 | Schneider et al. |
| 2006/0122454 A1 | 6/2006 | Riehl et al. |
| 2006/0218790 A1 | 10/2006 | Day et al. |
| 2007/0260107 A1 | 11/2007 | Mishelevich |

FOREIGN PATENT DOCUMENTS

| | | |
|---|---|---|
| EP | 1326681 B1 | 1/2007 |
| WO | WO 1999/039769 A1 | 8/1999 |
| WO | WO 99/55421 A2 | 11/1999 |
| WO | WO 02/09811 A1 | 2/2002 |
| WO | WO 02/32504 | 4/2002 |
| WO | WO 03/082405 | 10/2003 |
| WO | WO 2005/000153 A2 | 1/2005 |

OTHER PUBLICATIONS

Yiftach Roth et al., "A Coil Design for Transcranial Magnetic Stimulation of Deep Brain Regions", Journal of Clinical Neurophysiology, 2002, pp. 361-370, vol. 19, No. 4.

Kent R. Davey et al., "Suppressing the Surface Filed During Transcranial Magnetic Stimulation," *IEEE Transactions on Biomedical Engineering*, Feb. 2006, vol. 53, No. 2, pp. 190-194.

Sackheim, H.A., Commentary: Magnetic Stimulation Therapy and ECT, *Convulsive Therapy*, (1994), vol. 10, No. 4, pp. 255-285.

Barker et al.; Non invasive magnetic stimulation of the human motor cortex; Lancet; vol. 1; pp. 1106-1110; 1985.

Basser et al.; Stimulation of myelinated nerve axon by electromagnetic induction; Medical & Biological Engineering and Computing.; vol. 29; pp. 261-268; 1991.

Bohning et al.; Mapping transcranial magnetic stimulation (TMS) fields in vivo with MRI; NeuroReport; vol. 8; No. 11; pp. 2535-2538; Jul. 28, 1997.

Conca et al.; Effect of chronic repetitive transcranial magnetic stimulation on regional cerebral blood flow and regional cerebral glucose uptake in drug treatment-resistant depressives. A brief report; Neuropsychobiology; vol. 45; No. 1; pp. 27-31; 2002.

Davey et al.; Modeling the effects of electrical conductivity of the head on the induced electrical field in the brain during magnetic stimulation; Clinical Neurophysiology; vol. 114; pp. 2204-2209; 2004.

Davey et al.; Prediction of magnetically induced electric fields in biologic tissue; IEEE Transactions on Biomedical Engineering; vol. 38; pp. 418-422; 1991.

Hovey, C. et al.; The new guide to magnetic stimulation; The Magstim Company Ltd.; Carmarthenshire, United Kingdom; 2003.

Martin et al.; Transcranial magnetic stimulation for treating depression; Cochrane Review; 2002 (In (eds.): The Cochrane Library. Oxford: Update Software: The Cochrane Library. Oxford: Update Software.).

Ohnishi et al.; rCBF changes elicited by rTMS over DLPFC in humans; Suppl Clin Neurophysiol.; vol. 57: pp. 715-720; 2004.

Ruohonen et al.; Focusing and targeting of magnetic brain stimulation using multiple coils; Medical & Biological Engineering and Computing; vol. 35; pp. 297-301; 1998.

Ruohonen et al.; Theory of Multichannel Magnetic Stimulation: Toward Functional Neuromuscular Rehabilitation; IEEE Transactions on Biomedical Engineering; vol. 46; No. 6; pp. 646-651; Jun. 1999.

Ruohonen, J.; Transcranial magnetic stimulation: modelling and new techniques; (doctoral dissertation); Helsinki Univ. of Tech.; Dept. of Eng. Physics and Mathematics; Espoo, Finland; 1998.

Speer et al.; Opposite effects of high and low frequency rTMS on regional brain activity in depressed patients; Biol. Psychiatry; vol. 48; No. 12; pp. 1133-1141; Dec. 15, 2000.

Traad, Monique; A Quantitative Positioning Device For Transcranial Magnetic Stimulation; Engineering in Medicine and Biology Society; 1990; Proceedings of the 12th Annual Int'l Conf. of the IEEE; Philadelphia, PA; p. 2246; Nov. 1-4, 1990.

Vayssettes-Courchay et al.; Role of the nucleus tractus solitarii and the rostral depressive area in the sympatholytic effect of 8-hydroxy-2-(di-n-propylamino)tetralin in the cat; Eur. J. Pharmacol.; vol. 242; No. 1; pp. 37-45; Sep. 21, 1993.

Wasserman et al.; Therapeutic application of repetitive magnetic stimulation: a review; Clinical Neurophysiology; vol. 112; pp. 1367-1377; 2001.

Wasserman, E. M.; Risk and safety of repetitive transcranial magnetic stimulation: report and suggested guidelines from the International Workshop on the Safety of Repetitive Transcranial Magnetic Stimulation, Jun. 5-7, 1996; Electro-encephalography and Clinical Neurophysiology; vol. 108; pp. 1-16; 1998.

\* cited by examiner

ROBOTIC APPARATUS FOR TARGETING AND PRODUCING DEEP, FOCUSED TRANSCRANIAL MAGNETIC STIMULATION

BACKGROUND OF THE INVENTION

The present invention relates to electromagnetic stimulation of target areas, typically within the anatomy of a living organism such as a human medical patient or an animal. More specifically, the invention relates techniques for utilizing time-dependent and space-dependant variables to focus electromagnetic energy on a target area.

Transcranial Magnetic Stimulation (TMS) and Repetitive Transcranial Magnetic Stimulation (rTMS, a variant of TMS in which electromagnetic fields are produced in trains of multiple short pulses) have shown the ability to trigger neuronal firing in selected superficial brain regions. In at least one psychiatric condition (major depression), this effect of TMS and of rTMS appears to constitute an effective therapy. TMS and rTMS instrumentation are currently limited by their inability to focus their magnetic fields at depth. This is chiefly because a magnetic field always diminishes as a function its distance from the source.

Attempts have been made to focus electromagnetic energy into deep structures without overwhelming superficial structures. For example, it has been suggested to simultaneously use multiple coils such that the magnetic fields converge at a chosen point (see Sackheim, HA. Magnetic Stimulation Therapy and ECT (Commentary) Convulsive Therapy, 1994, 10(4): 255-8). Even if feasible, the coordination of multiple coils (e.g., adjusting for a specific target) may make the results less than satisfactory.

In U.S. Pat. No. 6,572,528, the inventors propose the use of an adaptation of a 1.5 Tesla MRI scanner to produce some form of transcranial magnetic stimulation. Because the largest of the magnets on such a machine (the solenoid) remains stationary and at steady state while the programmable magnets (e.g., the head coil and the gradient coil) are of relatively low field strength, such a configuration may not be capable of targeting for performing selective stimulation of targeted deep brain structures while sparing superficial structures.

A variety of new electromagnet configurations have been developed by the Helsinki group (Ruohonen, J, Dissertation for Doctorate of Technology, Helsinki University of Technology, Espoo, Finland, 1998), which may be useful in the context of TMS for reaching to deeper structures. However, these static magnets pass the greatest portion of their energies through interposed proximal tissue, and hence cannot alone achieve deep TMS while sparing proximal tissue.

In the article "A Coil Design for Transcranial Magnetic Stimulation of Deep Brain Regions" (Roth, Y; Zangen, A; Hallet, M; Journal of Clinical Neurophysiology, 2002, 19(4): 361-370), the authors describe the "Hesed" coil shape, which reportedly has a less sharp drop-off in power with distance from the coil. Additionally, a configuration of multiple coils has been attempted to stimulate deep brain structures. (George, MS Stimulating the Brain, Scientific American, editor's inset window, page 72 Sep. 2003). As mentioned above, even if such an approach does prove to be feasible, it is also likely to be expensive and inflexible. For example, targeting different brain regions may require a different coil array and even targeting the same structure in two different individuals may require two different sets of hardware.

Both mechanical and computerized stereotactic neurosurgical image guidance systems such as the STEALTH STATION by Surgical Navigation Technologies, Inc., Broomfield Colo. (Division of Medtronic Inc.) have been fitted to TMS coils, in an attempt to better aim the magnetic field at the targeted structure. However these approaches have met with limited success because of the principle of electromagnetism that the electromagnetic field is always greatest next to the surface of the coil than it is at any given distance away from that coil. Hence, even when carefully aimed with expensive image guidance equipment, superficial neuronal structures continue to be overwhelmed before targeted deep structures can be stimulated.

There exist devices designed to distribute other forms of energy lightly to the proximal periphery, while concentrating it at a distal target point. U.S. Pat. No. 5,207,223 (Adler, JR, 1993) describes a method for manipulating a radiation beam source so that emitted radiation affects a target internal to the human body while minimizing peripheral radiation damage. U.S. Pat. No. 5,427,097 (Depp, JG 1995) provides further methodology for this purpose and the CyberKnife® device (Accuray, Inc., Sunnyvale, Calif.) is a radiosurgery robot that functions using the technologies described in those patents.

Magnetic fields differ from radiation beams in the manner that they emanate from their sources, their physical parameters, the methods by their parameters may be altered, and the manner in which they affect living tissue to achieve a desired effect. Consequently, satisfactory techniques by which magnetic field sources can be moved and otherwise manipulated in real time so as to selectively affect deep targeted structures while leaving superficial structures relatively undisturbed and avoiding undesirable side effects such as seizures have not been developed. Additionally, it would beneficial to provide repetitive transcranial magnetic stimulation that can selectively stimulate deep brain tissue without overwhelming superficial cortical brain structures. Further, robotically manipulating TMS sources and automatically altering their magnetic field parameters as a function of the instantaneous coil location relative to the designated target would be desirable. Finally, it would be beneficial to have transcranial magnetic stimulators that are able to stimulate or suppress arbitrarily selected neuronal areas by changing numerically or graphically selected target coordinates.

SUMMARY OF THE INVENTION

The present invention provides techniques for applying electromagnetic energy to deep, targeted areas without overwhelming other areas (e.g., areas more proximal to the magnetic field generators such as coils). In general, one or more coils are moved relative to a target area and magnetic fields are applied to the target from multiple coil locations. As a result, the aggregate electromagetic energy applied to the target over a finite period of time is greater than the energy delivered to interposed regions.

Aspects of the invention include exploiting the time-dependent and space-dependant variables of repetitive transcranial magnetic stimulation to effectively focus a magnetic field at depth. By delivering a magnetic field or train of magnetic pulses in the manner described herein, the energy may be concentrated at depth within the human brain and targeted structures may be directly activated in a precise and deliberate manner. In addition to targeting the desired structure, the approach avoids over-stimulating other structures that could cause undesirable effects such as seizures. Additionaly, the embodiments of the inveention may be valuable tools for neuroscience research and may provide therapies for certain neuropsychiatric conditions.

In one aspect of the invention, Cartesian or polar coordinates are stereotactically obtained for a specific target region (specific neurological structure that one wishes to depolarize)

within an orbital volume within which the structures of interest are contained (e.g., human head or phantom, and their sub-regions). This may be accomplished using MRI studies from that specific patient and/or stereotactic atlas, and these types of data may be graphically or physically applied to a testing and planning "phantom" model. Stereotactic instrument navigation, software, and other tools as are known in the art may be used to facilitate correlation between patient image data sets, stereotactic atlases, and the real-time location of instruments including magnetic coils.

In another aspect of the invention, one or more TMS or rTMS coils are robotically moved in one or more specific manners, external to, but within the vicinity of the region that one wishes to selectively stimulate. In one embodiment, this movement is a carefully metered time/distance continuous orbit around the volume of a patient's head ("a component of the orbital volume"). Alternatively, the movement may be linear, forward-and-back, semicircular, oscillating, or other motion.

In another aspect of the invention, electromagnetic field parameters are modified as a function of distance to the target and the nature of the interposed tissue. For example, if the path is to be orbital, the strength of the magnetic field or field pulses emitted by the coil may be modulated in real time inversely to the square of the distance from the target region within the orbital volume. The magnetic field may also be turned off when the coil is at a particular location in its path of travel such that EMF may not reach the target structure without unintentionally affecting other structures along or near the interposed vector. Other magnetic-field characteristics may also be modified at specific orbital locations during coil movement.

In this manner, over the course of one or more orbits, paths or passes, the effect is to distribute the net magnetic stimulation lightly (sub-action potential-threshold) in the periphery, while concentrating the stimulation (supra-action potential-threshold) within the target structure. In addition to the magnitude of the magnetic field, the frequency of stimulation will determine its impact.

Additionally, in another aspect of the invention, a design for a testing and treatment planning "phantom" model is described. The phantom allows users to assess the degree of targeting and local field strength that is achieved. Electrically active physical models of nerve bundles and tracts running through the phantom may be used to evaluate the performance of the current invention at different settings, so as optimize configuration for a particular procedure being planned. By mapping stereotactic atlas data, or actual patient-specific scans or scan-derived data, to the phantom volume, generic, or patient-specific treatment planning may be accomplished.

In one embodiment, the invention provides a method of applying electromagnetic energy to a target. A coil is moved relative to the target. Current is applied to the coil while it is at multiple locations in order to direct magnetic fields to the target such that the magnetic field energy over time is higher at the target than areas around the target. The target can be an area in a patient's body (e.g., brain or nervous system) or a testing phantom.

In another embodiment, the invention provides a method of applying electromagnetic energy to a target. A coil is rotated relative to the target, meanwhile continuously re-angled to remain perpendicular to the target trajectory throughout the orbit. The position of the coil is adjusted so that magnetic field energy from the coil will be greater at the target than magnetic field energy at areas near the target at the same distance to the coil. Current is applied to the coil while it is at multiple locations in order to direct magnetic fields to the target such that the magnetic field energy over time is higher at the target than areas around the target.

In another embodiment, the invention provides a method of measuring electromagnetic energy. Measurements of electromagnetic energy at a plurality of locations over time are received. Electromagnetic energy at a location over time is determined and the electromagnetic energy at the location over time is compared to a threshold. Additionally, an indication can be made to the user that the threshold has been crossed.

In another embodiment, the invention provides an apparatus for measuring electromagnetic energy. Multiple sensors for measuring electromagnetic energy are utilized along with one or more sensors that is designed to represent a physical structure in a patient. For example, the physical structure can be an axon bundle.

In any of these embodiments, the frequency of stimulation can be varied as well as the magnitude to build up stimulating or inhibitory impacts. Other features and advantages of the invention will become readily apparent upon review of the following description in association with the accompanying drawings.

DETAILED DESCRIPTION OF PREFERRED EMBODIMENTS

Figure 1:
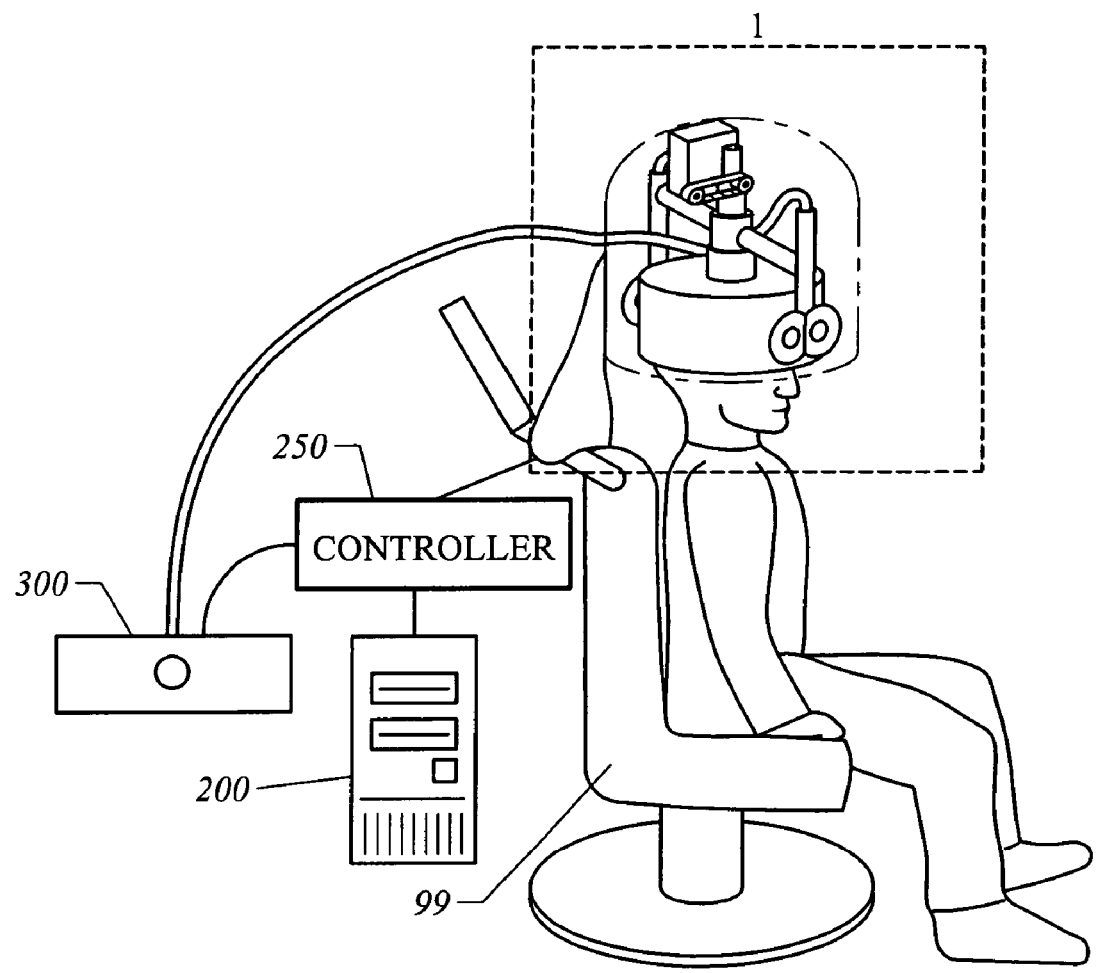
FIG. 1 shows an embodiment of a robotic system for targeting and producing transcranial magnetic stimulation.

In the description that follows, the present invention will be described in reference to embodiments that utilize computers and electromechanical devices to focus electromagnetic energy to target areas. More specifically, the embodiments will be described in reference to preferred embodiments. However, embodiments of the invention are limited to any particular configuration, architecture, or specific implementation. Therefore, the description of the embodiments that follows is for purposes of illustration and not limitation.

Historically the magnets used for Transcranial Magnetic Stimulation (whether single pulse or repetitive (so called rTMS)) produce magnetic fields that affect superficial structures (those close to the magnets) and not deep structures. Impacting deeper structure cannot be practically achieved to by simply increasing the strength of the magnetic field. The field strength of a magnet falls off rapidly with distance (one over the square of the distance). Increasing the magnetic-field intensity sufficiently to cause demonstrable effects on deep structures stimulates the superficial neural structures to such an increased extent that undesirable side effects such as unintentional seizures can occur. One method for attempting to impact deeper structures without unduly impacting superficial structures is to use specially shaped electromagnets such as the Hesed design cited above.

Embodiments of the current invention use a different approach—that of moving a magnet in a precise manner, external to the patient's head such that, over a brief but finite given period of time, the brain surface at any given point receives only a small amount of magnetic energy. At the same time, because of the precise control of the position and orientation of the magnet, the target structure remains within the path of the electromagnetic field for a much greater period of time. Hence, the target structure, cumulatively over a time period, receives a much larger amount of energy than does any of the brain tissue superficial to it. Thus, the target structure may be stimulated above action potential threshold, while leaving the superficial cortical structures undisturbed, below action potential threshold.

In some embodiments, this movement may be a circular or semi-circular orbit about the patient's head. The electromagnetic field emitters themselves can be of a variety of physical shapes (e.g., circular, figure-eight, "slinky", double cone, solid core, etc.), and may be coil, or non-coil technologies. The plane of rotation can be moved in the vertical direction and the radius of the orbit and eccentricity with respect to the center of the mass of tissue being stimulated (e.g., the brain), and the tilt in any direction can be adjusted as well. Note that the target is not necessarily a point, but may be a structure (such as a nerve tract or neural nucleus), and that structure may be irregularly shaped (like a bent bundle of neuronal axons). Farther, the head need not be centered within the apparatus (e.g., rotating electromagnet(s) generating the magnetic field. It can be offset to one side. Thus a target offset from the center point of the head in planar view can placed at the center of the orbit of rotating electromagnet(s), rather than the center of the head being located there.

The system works efficiently because like examples using radiation, the target is being intensely energized during a significant portion (perhaps all) of the orbit, while the surrounding tissue is being swept through relatively more rapidly and thus at significantly lower intensity. Targets may be located outside the cranium, such as (but not limited to) the spinal cord, peripheral nerves in limbs, and the heart. Examples of extra-cranial functionality to be modified through stimulation are exciting neural activity (which, for example may include causing muscles to twitch), inhibiting neural activity, or controlling cardiac arrhythmias. With respect to frequency of stimulation, pulses at one Hz. or less have been shown in some studies to have an inhibitory effect while a rate above that (e.g., 4-8 Hz. stimulation may disrupt speech) tends to be excitatory. At higher frequencies (say 50-60 Hz. or more), one may elicit seizures in susceptible people (such as those with epilepsy). The specific magnetic-field strength and pulse rate that will actually be used in the context of the present invention will be empirically determined for any given target region.

This mechanism of the current invention provides for increased flexibility because the configuration can be adjusted to stimulate deeper structures in a variety of locations by adjusting the orbit and orientation of the stimulating electromagnet (or orbits and orientations of two or more stimulating electromagnets). In certain applications, a chain of events is involved as follows.

The current through the stimulating coil causes a magnetic field pulse with an associated rate of change in magnetic field that induces an electric field impacting the neurons that induces current in the nerve tissue. Since neurons leak (i.e., are not "perfect capacitors"), a rapid change in the magnetic field is important because there is less time for the neurons to lose charge and the impacts of successive pulse can be added. Biphasic pulses have been shown to be more effective than monophasic pulses because (a) more energy is returned to the capacitor driving the electromagnets so less "external recharge" is mandatory and (b) lower field intensities are required to induce currents in neurons. Effective stimulation depends not just on the intensity of the magnetic field, but its rate of change as well. For this reason, the movement of the coil alone, even as it emits pulses, will result in stimulation of the underlying nerve axons.

Figure 9:
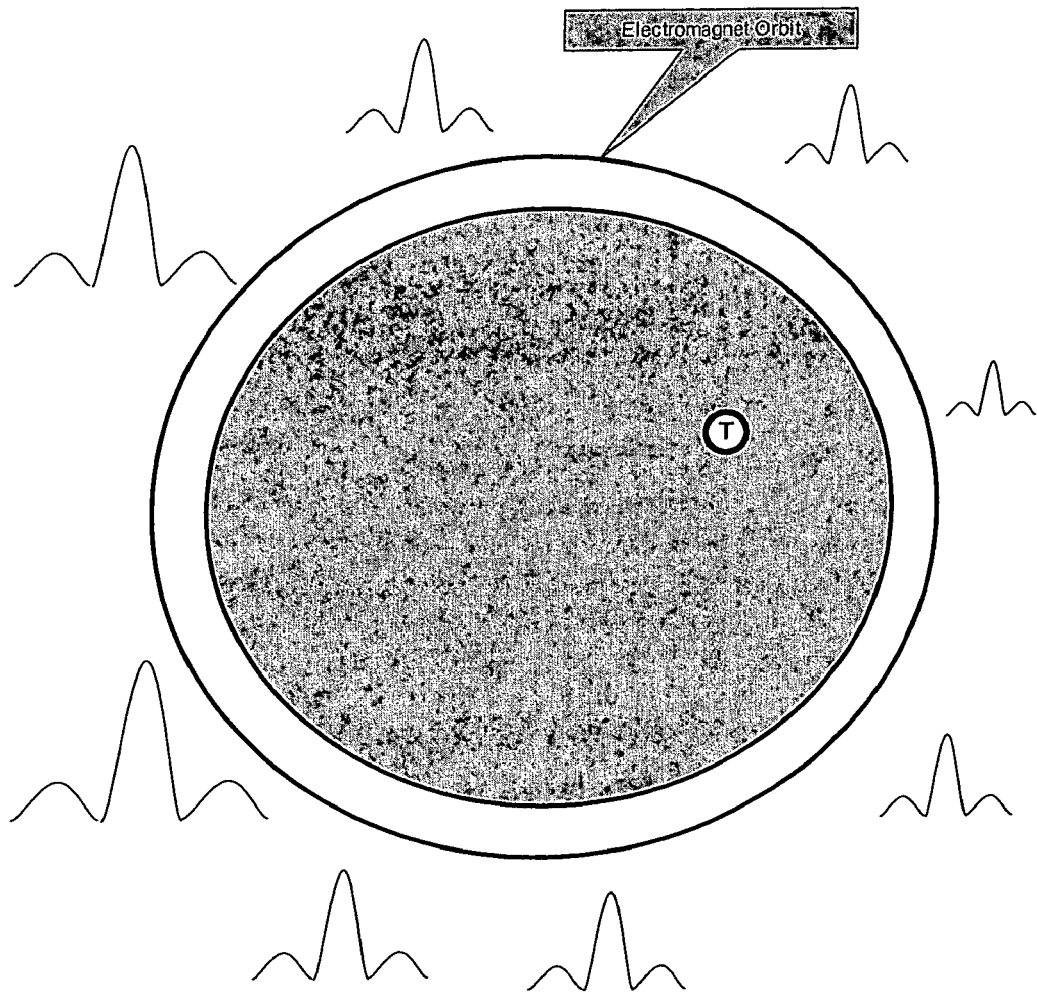
FIG. 9 shows a method of adjusting the energy applied to a magnetic coil as a function of its position in orbit around a target.

Further, the magnetic field does not have to be same during an entire orbit. One can vary field strength as a function of the position in the orbit as shown in FIG. 9. For example, a lower intensity can be used when the target is closer to the orbital path and a higher intensity used when the target is further away. This would allow, for example, a constant intensity to be maintained at the target locations in cases (the most frequent ones) in which the target is not located at the exact center of the orbit. Besides modulating the intensity of the generated field, the direction of the magnetic field can be reversed, if applicable. When multiple electromagnets are employed, they will not necessarily rotate in the same orbit or have the same orientation. Interactions among the electromagnetic fields produced by multiple magnets provides the ability to do refined field shaping so the net profile can be modified and controlled. Resultant fields can focused in 2D or 3D and have vertical orientations, horizontal orientations or any combination in between.

FIG. 1 shows mechanical portion 1 as one embodiment of the portion of the invention that holds the motor and apparatus that moves the coils, and which lies physically closest to the patient. Details of mechanical portion 1 will be described in more detail in FIG. 2. Mechanical portion 1 is mounted on sturdy medical procedure chair 99.

Contained within mechanical portion 1 are magnetic coils which are moved about by actuators under the precise mandates of a control system The rotational step-motors and linear actuators, described in detail in subsequent figures, receive electrical power pulses from a device controller array 250. Device controller array 250 is an assembly of one or more moving device controllers. An exemplay device controller arrary is the StepperWorld FET-3 three-channel controller board (www.stepperworld.com, Los Angeles, Calif.). Other components that may reside in device controller unit 250 include relays, high-capacity transistors, potentiometers, resisters, and zener diodes, for adjusting the current that flows to the coils at any given moment.

Stepper motors controlled by device controller array 250 may serve to physically move coils relative to the target and also to adjust coils so they direct electromagnetic energy to the target. Additionally, the stepper motors may serve to modulate coil function, for example by turning the axis of a high-capacity potentiometer in order to automatically adjust current flowing to the coils to compensate for distance to target. Finally, device controller array 250 may contain batteries or capacitors for taking up excess current that is shunted away from the coils, which may be subsequently returned to a TMS generator 300.

The individual device controllers residing within device controller array 250, in turn, may be controlled by a custom software application adapted from the StepperWorld Stepper-Motor Control Panel Application software environment, which runs on Windows 98, and resides on a computer 200. This same application may be used to control the rate of pulses delivered to each of the motors. The program maintains the relationships among the movements and positions of the stepper motors and uses internal models of the physical regions to be stimulated or avoided. By controlling the action of high-capacity relays, High Voltage Insulated Gate Bipolar Transistors (HVIGBTs), or high-capacity potentiometers/resistors contained within controller device array 250, the software application appropriately regulates the power of the pulses, interval between pulses and the frequency content of the pulses driving the stimulating the electromagnets as a function of the locations of those electromagnets relative to the target region.

Communication between computer 200 and controller device array 250 can be through the parallel port of the computer. Typical stepper motors are of the unipolar type with 1.8 degrees of rotation per step (equaling 200 steps per complete revolution).

At the start of each sTMS session, the coils are generally aligned in three dimensions at an "initialization" position graphically marked on the shell. The coils are then physically locked into a precise position by inserting a ¹⁄₁₆" diameter cylindrical steel "key" through an aperture on coil, which extends into the inner wall of the shell. With the coils now in the Initialization position, the software control system calibrates the rotational position of the step motor and linear actuators, and the locking initialization key is removed. Subsequently, during that session the precise positions of the electromagnet coils are known, since any given coil position may be found at a predetermined number of steps from the initialization position. Position sensors or encoders, such as optical encoders are also usable, as is know in the art, to ensure the proper location of the coils at any given time, and are particularly useful if servo-type actuators are used in place of step actuators.

Also shown in FIG. 1, TMS generator 300 serves electrical power to the magnetic coils within mechanical portion 1, according with voltage, current, pulse frequency and other electrical characteristics (described in more detail in the discussion of FIGS. 7 and 8) controlled in real time by software on computer 200.

Figure 2:
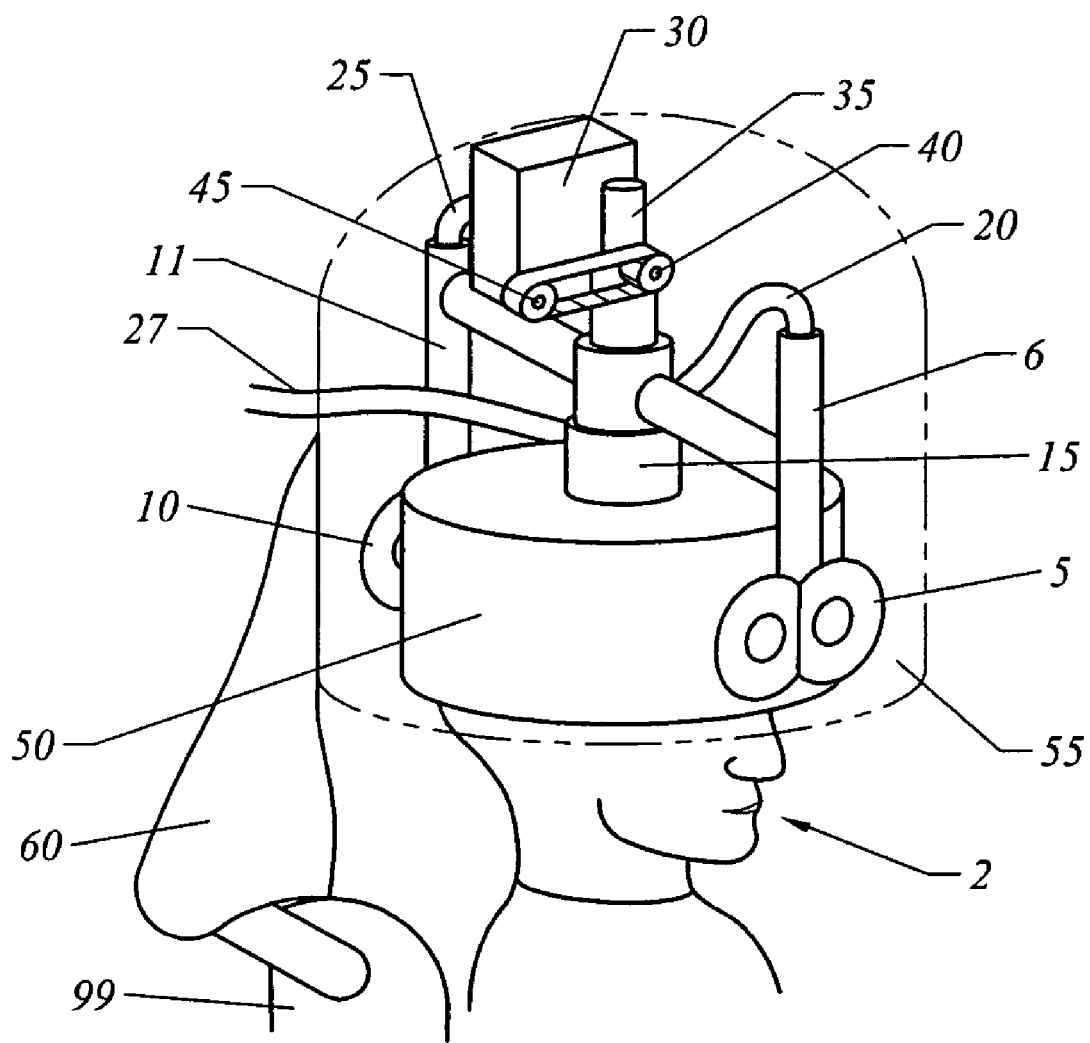
FIG. 2 shows detail of a mechanical portion of the system of FIG. 1.

FIG. 2 shows detail of mechanical portion 1 from FIG. 1. As a patient sits in chair 99, patient's head 2 is placed within the mechanical portion between magnetic coils 5 and 10. Additional magnetic coils may also be used as well as embodiments where one or more coils are utilized without opposing coils. Coils 5 and 10 are shown as the figure-eight type design. In this embodiment, they are held at 180 degrees from one another by telescoping radial extension shafts 7 and 8.

Linear actuators 6 and 11 couple the extension shafts 7 and 8 to the coils 5 and 10. As shown, linear actuators 6 and 11 run perpendicular to the extension shafts. The linear actuators are motors that operate along a straight trajectory. These allow the position of the magnetic coils to be independently adjusted in their vertical dimension (how high up and down the sides of the head) during movement.

Radial extension shafts 7 and 8 turn about a central axis created by the presence of a slip ring 15. In the case of the embodiment illustrated, slip ring 15 is an 8-conductor slip ring, and thus can maintain an uncompromised electrical connection for the coils and for linear actuators 6 and 11 throughout their movement about the axis. The slip ring may be solid or with a central channel, the latter facilitating the passage of air or liquid cooling systems into the interior of the apparatus.

Coil power cables 20, 25 bring current from TMS generator 300, in accordance with energy parameters dictated in real time by the software residing within computer 200, and modified within controller device array 250. For example, automatically dialed potentiometers may be interposed in between TMS generator 300 and the coils, and in one embodiment within coil power cables 20 and 25.

Cable 27 delivers power for magnetic coils 5, 10, motion control and power for a stepper motor 30, and motion control and power for linear actuators 6, 11.

Stepper motor 30 turns the radial extension shafts 7 and 8, and thereby rotates magnetic coils 5 and 10. This rotation is done under the control of software residing on computer 200 and controller device array 250. A timing/drive belt may be used to couple step motor gear 45 on the shaft of step motor 30 to drive shaft gear 40 on drive shaft 35. Drive shaft 35 is connected at a right angle to radial extension shafts 7 and 8 (see FIG. 3A). In this manner, the repeated stepping of step motor 30 causes a corresponding orbital movement in the radial extension shafts, and hence coils 5 and 10.

Covers may be placed around the path of the apparatus, and in the embodiment shown in FIG. 2, might look similar to the salon hair-drying machines that were popular in the 1950s. The cover consists of an inner shell 50, which serves to protect the patient from any possible strike or heat from the apparatus, and an outer shell, 55, which may serve to keep dust, fingers, and other foreign objects out of the mechanism, as well as for its cosmetic value.

A support strut 60 serves to anchor the head-mounted mechanism to chair 99 so that it is mechanically stable, and so that the patient's head need not bear any weight.

Figure 3A:
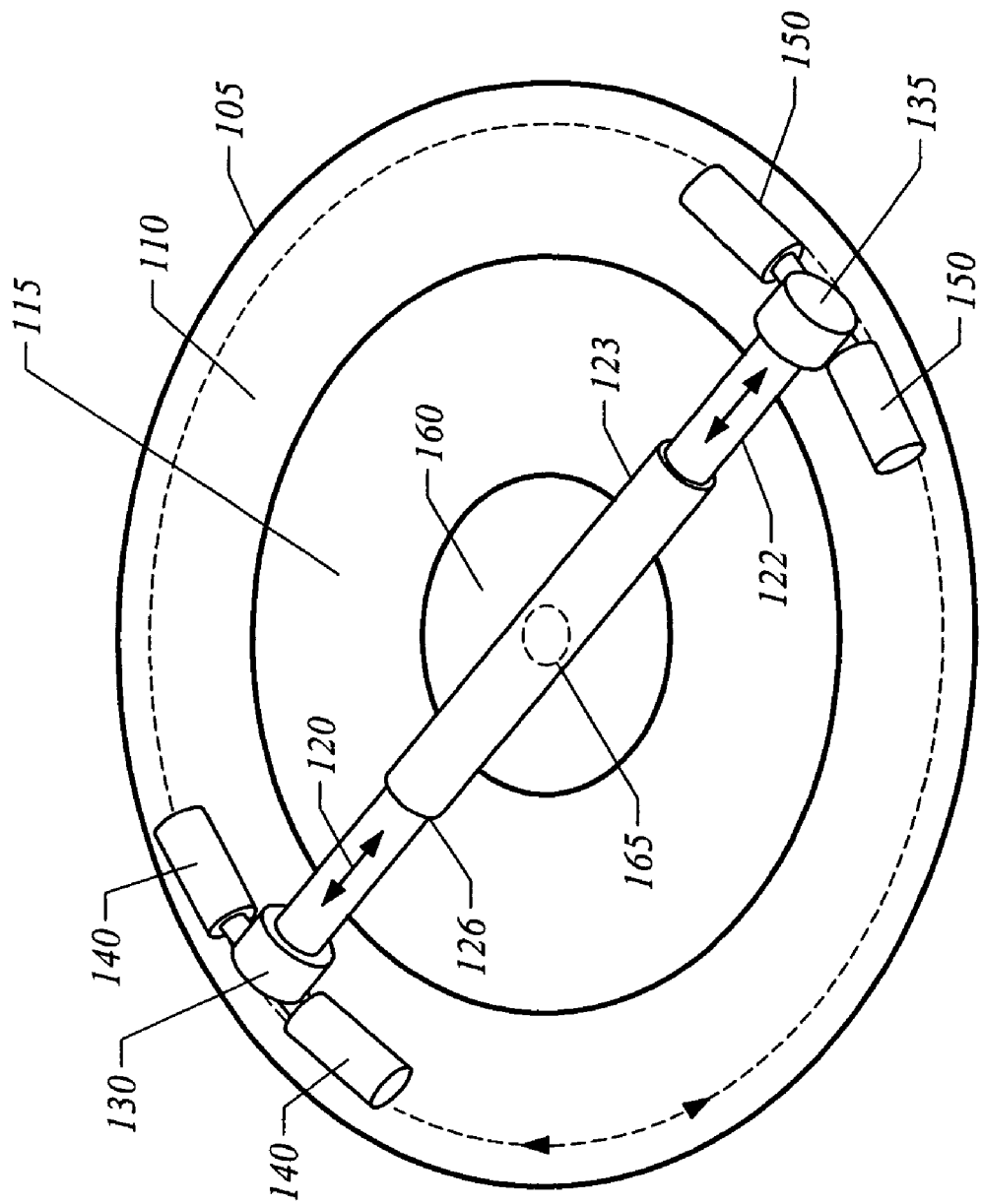
FIG. 3A illustrates a cut-away axial view of the mechanical portion of FIG. 2 from below.

FIG. 3A shows a cut-away axial view of the mechanism of FIG. 2 as it would appear from below. One or multiple magnetic coils may be used within the scope of this invention, and in this case, two magnetic coils at are shown extended radially at 180 degrees from each other. When multiple rotating electromagnets are used, one should avoid magnet coils colliding with each other and not have the orbit of one block the magnetic field of any other. In addition, the configuration should allow for EEG recording to monitor status or participate in control of the stimulation process as well as permit use of imaging devices such as functional MRI. Provisions for these needs are provided herein.

In FIG. 3A, magnetic coils 140 and 150 are rotated by telescoping radial shaft components 120, 122 and 123. The telescoping function allows the radial shafts to shorten for to accommodate non-circular orbits. For example, the human head is typically elliptical as opposed to circular and thus energy utilization in elliptical orbits is more efficient because the electromagnets are closer to the head. In other applications, non-circular orbits could potentially be used to create more targeted stimulation, particularly in cases where one wants to avoid a sensitive area that could be damaged with serious consequences.

Central common portion of the telescoping radial shaft 123 pivots about at a central point of drive shaft 165 (drive shaft 35 in FIG. 2), which is affixed to radial extension shaft common portion 123 perpendicular to its long axis. Pivot shaft 165 is affixed to the rotating core of slip ring 160. Slip ring 160 may be of solid or hollow core, the latter being useful for passing air cooling flow through to apparatus head space 115, or within the magnet channel located between inner shell 110 and outer shell 105. Head space 115 is created the area encircled by inner shell wall 110. Linear actuators 130 and 135 are shown in cross section, correspond to those shown along a lateral view in FIG. 2, and serve to move the coils above and below the plane of the FIG. 3A, and hence adjusting their axial (height) position along side of the patient's brain.

Figure 3B:
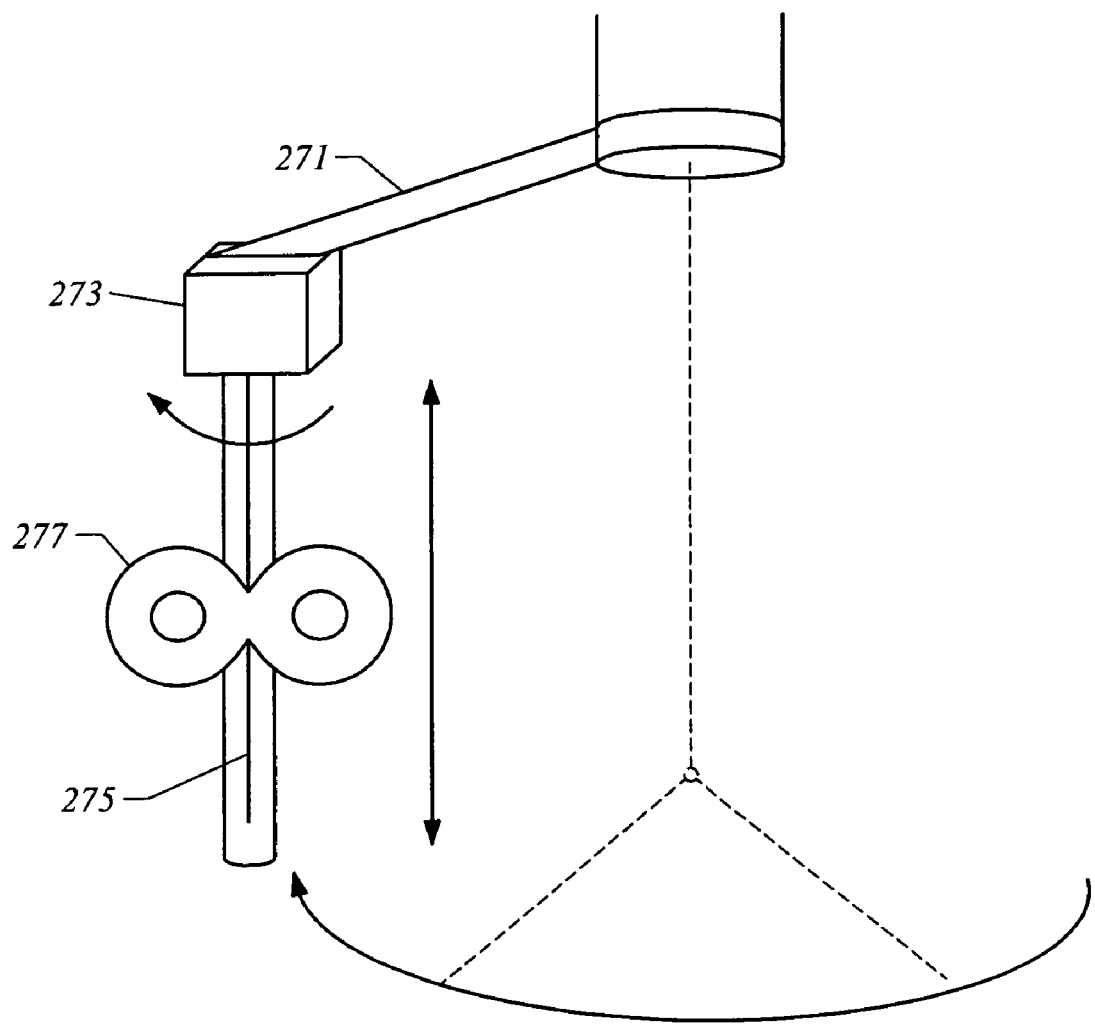
FIG. 3B shows an embodiment of the rotational members that can be directed to position the coils at a desired three-dimensional location and focusing direction.

FIG. 3B shows an embodiment of the rotational members that can be directed to position the coils at a desired three-dimensional location and focusing direction. A rigid strut 271 (which can alternatively include a linear actuator as shown in FIG. 3A) is rotated about a vertical or y-axis as described above. A rotational step motor 273 is positioned at the end of rigid strut 271.

A linear actuator 275 is connected to and rotatable by step motor 273. As shown, coils 277 are attached to linear actuator 275. Step motor 273 allows coils 277 to be rotated with an axis parallel to the vertical or y-axis, while linear actuator 275 allows coils 277 to be moved up and down in the vertical or y-axis. The different combinations of possible movement of the coils allow the coils rotate around the target, vary the distance to the target, vary the elevation of the coils, and vary the direction the electromagnetic energy from the coils is focused.

Figure 3C:
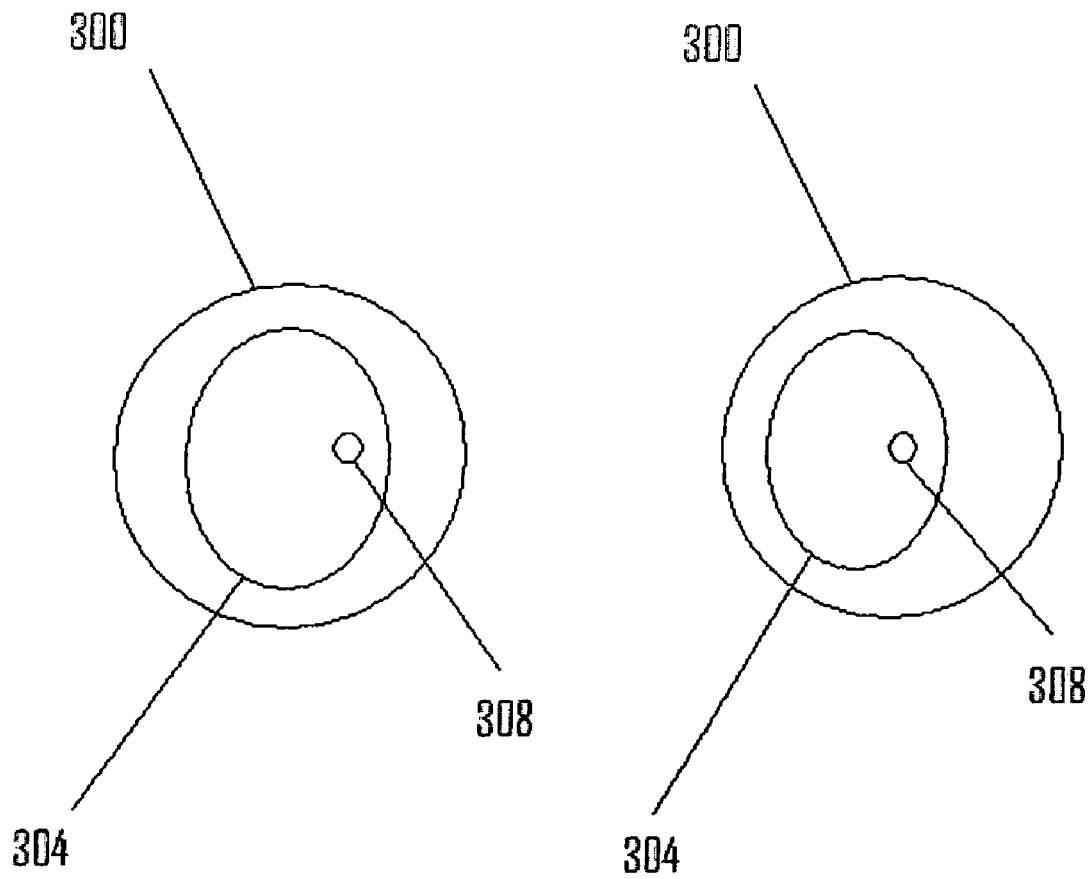
FIG. 3C illustrates different positions of target areas and operating characteristics that may be adjusted.

FIG. 3C illustrates different positions of target areas and operating characteristics that may be adjusted. As shown, there are two cases of the position of a head 304 with a target lesion 308 relative to a magnetic field stimulating apparatus 300. Assume the magnetic field stimulating apparatus is comprised of rotating magnets as in FIG. 3A. The case on the left represents an application where the head of the patient is centered within the stimulating apparatus 300 and target lesion 308 is not at the center of the orbit of the rotating electromagnets.

The case on the right represents an application where the head of a patient is not centered within stimulating apparatus 300, but target lesion 308 is centered. In this configuration, the control of the magnitude and possibly frequency of the magnetic field generation may be simpler since the centered target is equidistant from opposite sides of the given orbit. Still, control must be exercised (including possibly turning down or off the magnetic field generation at certain points in the orbital position of the electromagnets) so critical areas that are not to be stimulated above a given threshold (or inhibited) will be spared.

Although the orbits are shown as circular in FIG. 3C, the orbits can be elliptical (or other shapes) in order to better focus the electromagnetic energy to the target. Embodiments of the invention allow the coils to be placed in a desired position in three dimensional space. Thus, the orbits are not limited to any particular shape and the shape can also be varied in real-time during operation.

Figure 4:
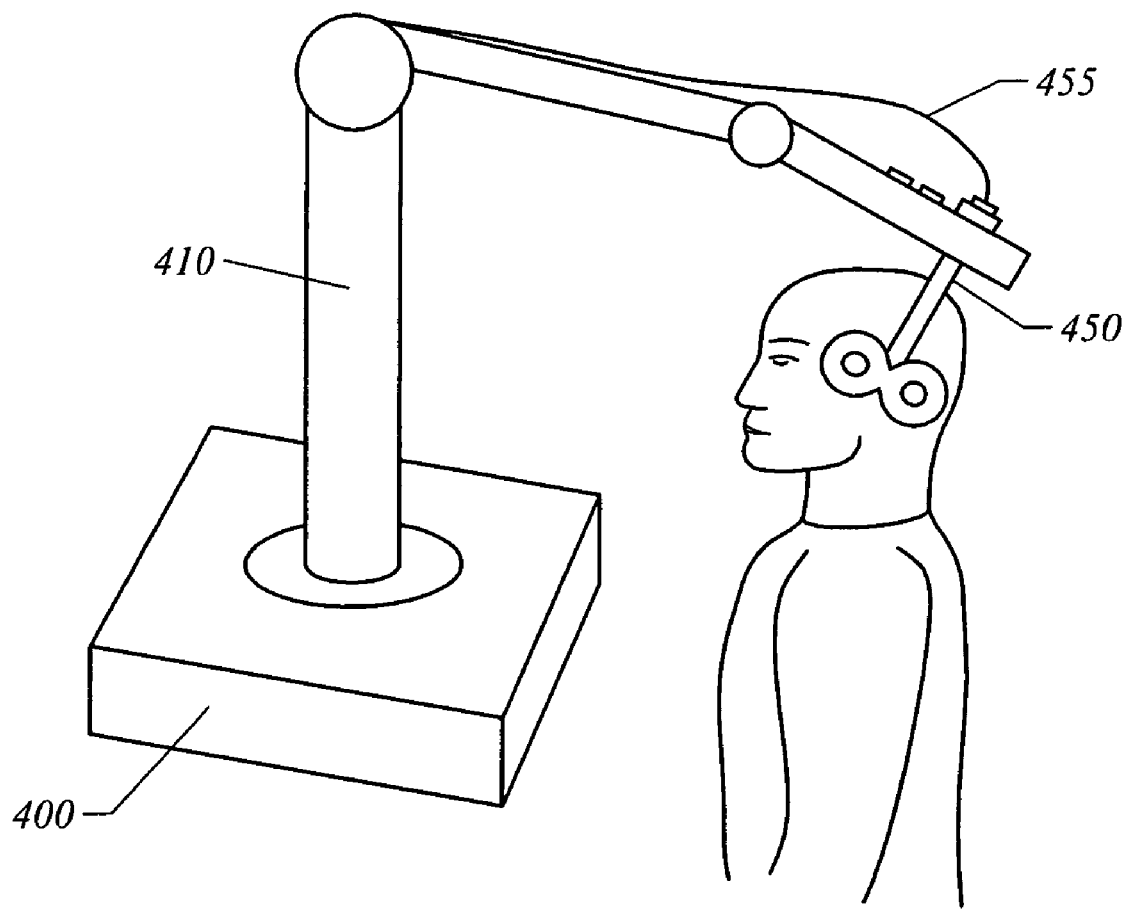
FIG. 4 shows another embodiment of a robotic system for targeting and producing transcranial magnetic stimulation.

Other configurations for the coil manipulating apparatus can also be designed for use with the invention. For example, FIG. 4 shows a standard multi-jointed industrial robot capable of gripping and manipulating objects with 6 degrees of freedom may also be used for the movement of one or more coils along orbital, oscillatory, linear, or other selected paths.

As shown, a robotic arm 410 is supported by a base 400. Robotic arm 410 manipulates coils 430 around a patient's head 450 to direct electromagnetic energy at a target area therein. Electrical cables 455 can supply the desired current to coils 430 to generate the desired magnetic fields.

Software and systems that could be adapted for the control of movement of such robots are also known in the art. One such example is the software used to control the CyberKnife® (Accuray, Inc., Sunnyvale, Calif.) radiosurgery systems. Although relatively standard multi-jointed industrial robots are used to control coil movement, magnetic field parameters may still need to be manipulated during the course of each treatment, those functions remaining under the control of mechanisms described in the descriptions of FIGS. 7 and 8.

Figure 5:
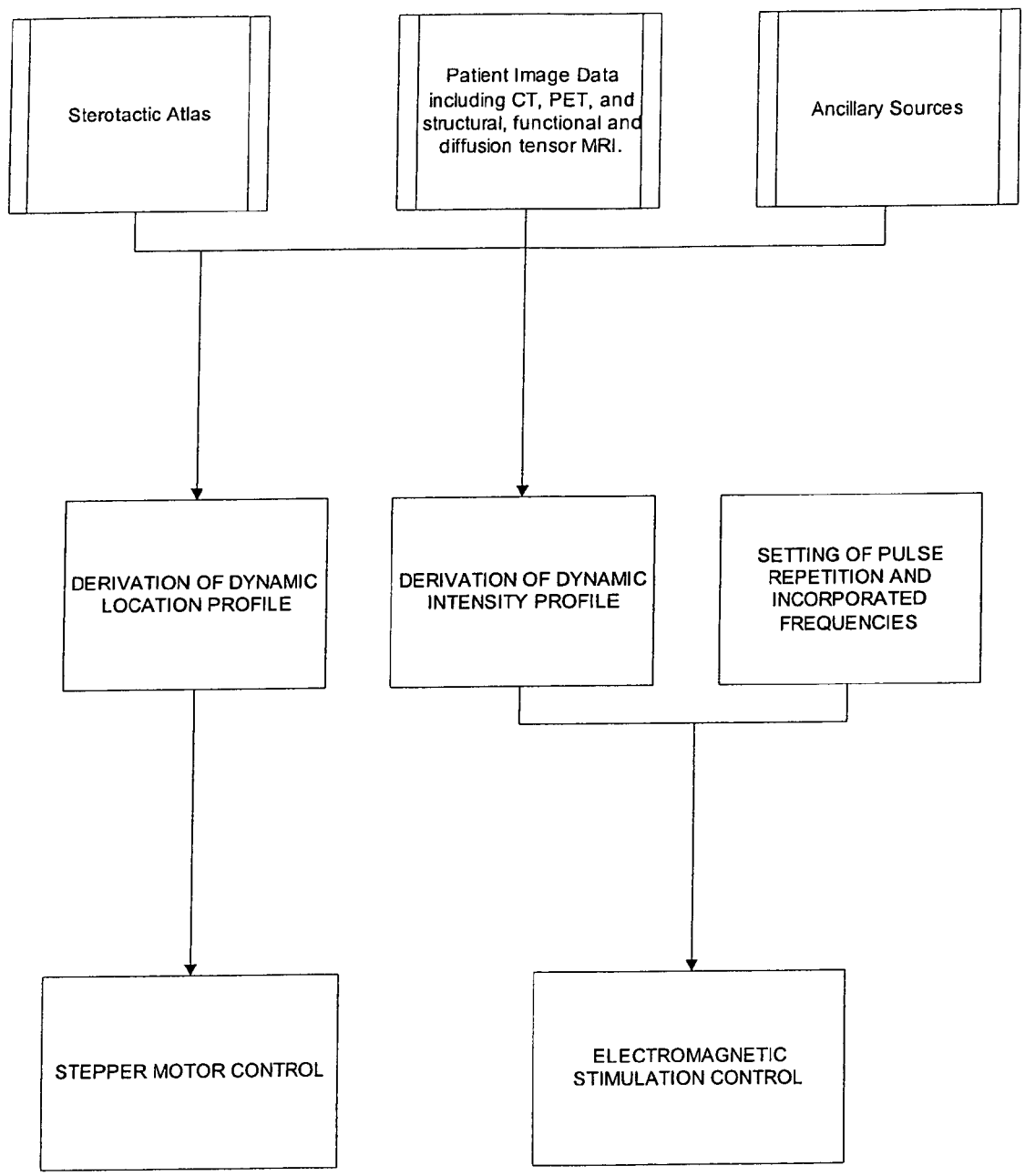
FIG. 5 shows a command and control structure of one embodiment of the invention.

FIG. 5 demonstrates one embodiment of a command and control structure. As noted previously, there are a number of variables that should be controlled during a given sTMS session. A characteristic of TMS is it provides resolution in both the spatial and temporal domains so it inherently includes a higher degree of command and control requirements than other systems. Derivation of the dynamic location profile is dependent on spatial information obtained from one or more of stereotactic atlas data, functional MRI or other images segmented manually or automatically to separate out "allowed regions" for interventions versus "not-allowed regions," and ancillary sources. The movement of the electromagnets controlled by the dynamic location profile in one embodiment is obtained through the use of stepper motors.

The derivation of the dynamic intensity profile is again dependent on stereotactic, segmented functional MRI or other medical images and ancillary sources. In one embodiment, this derivation plus the setting of pulse repetition (and the stimulation frequencies incorporated in the pulses) controls the electromagnetic stimulation. It is important to effectively combine the spatial location, field intensity and pulse/frequency characteristics of the stimulation to produce the desired result. This, of course, includes consideration of patient safety. It is to be noted that the described embodiment or alternative ones provide for delivery of magnetic field in a variety of formats (e.g., single pulses triggered periodically, pairs of pulses with variable or fixed inter-pulse separations, or trains of pulses delivered over a period of seconds). Parameters of the magnetic field that may be modulated are further described in the discussion of FIG. 8.

Target locations can be located by a technique such as a functional MRI. One can do calibration of location by seeing impacts on "known" adjacent areas. The present invention may be used in conjunction with other modalities such as electrical stimulation of implanted deep electrodes and psychopharmacologic agents. The electromagnetic stimulation may also be useful in order to heat a suitable implanted target.

Figure 6:
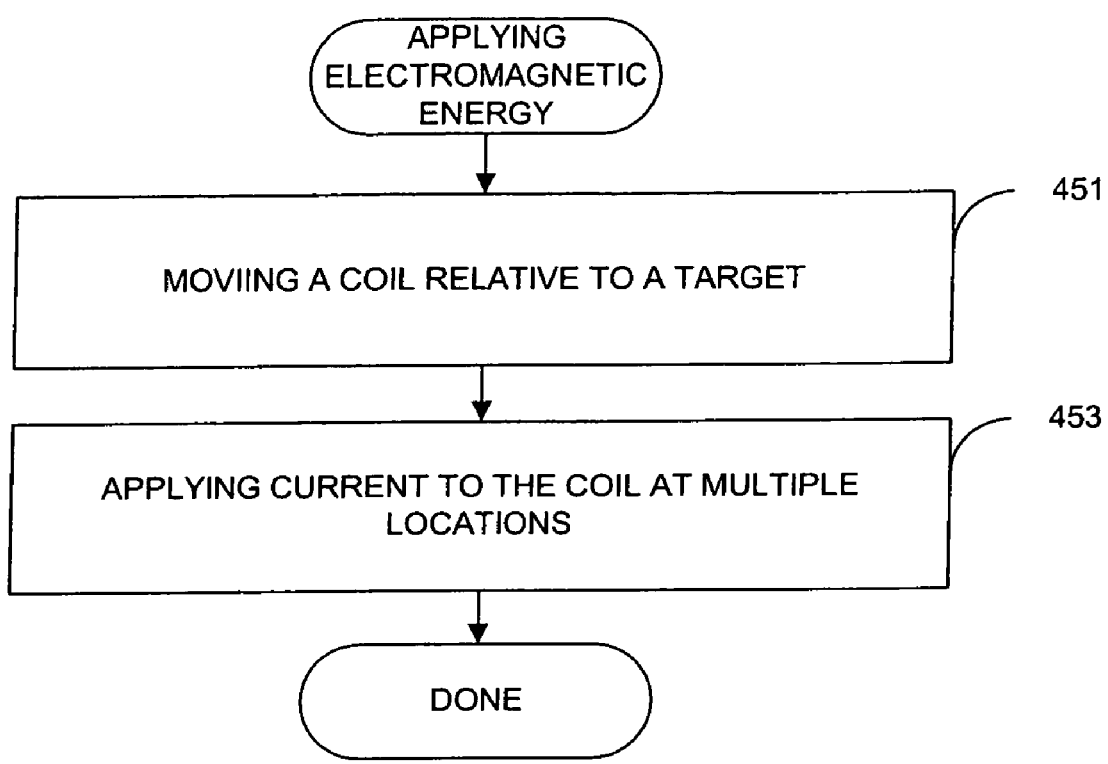
FIG. 6 shows a flow chart of a process of applying electromagnetic energy.

FIG. 6 shows a flowchart of a process of applying electromagnetic energy to a target. As with all flowcharts shown herein, steps can be added, deleted, reordered, and combined without departing from the spirit and scope of the invention.

At a step 451, a coil is moved relative to the target. As described above, the coil can be rotated (full or partial orbit), oscillated, rolled, pitched, moved linearly, or any other type of movement. A single coil can be used, multiple coils and even coils on opposing sides of the target as shown in FIG. 3.

Current is applied to the coil at multiple locations at a step 453. The current is applied in order to direct magnetic fields to the target such that the magnetic field energy over time is higher at the target than areas around the target. For example, this prevents areas between the coil and target, especially areas proximal to the coil, to be over exposed to electromagnetic energy.

Figure 7:
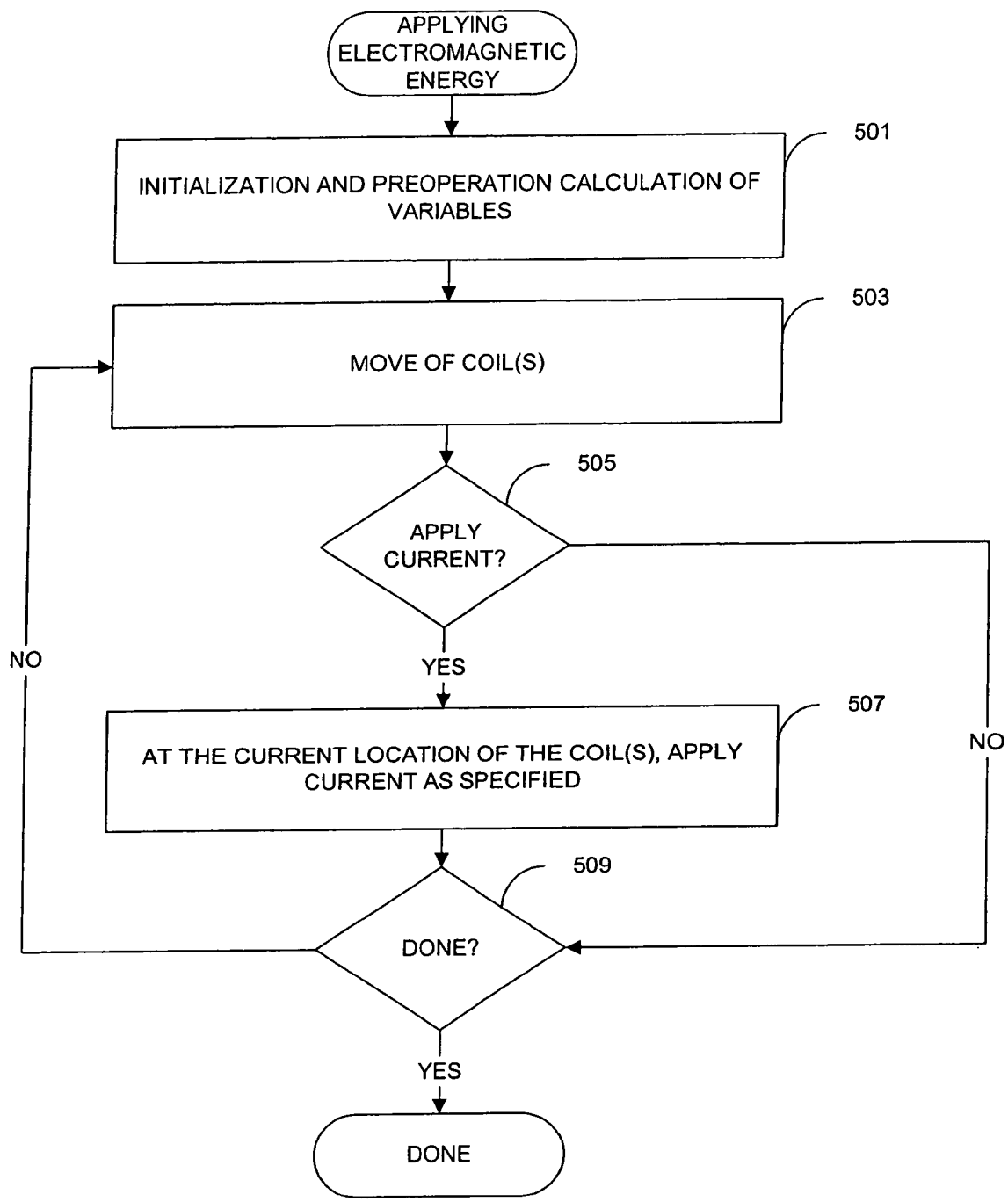
FIG. 7 shows another flow chart of a process of applying electromagnetic energy.

FIG. 6 shows a high level flow. Other variables are utilized in some embodiments so FIG. 7 shows a flowchart of another process of applying electromagnetic energy to a target that includes some other possible variables.

At a step 501, initialization and preoperation calculation of variables is performed. Initialization can include initializing the hardware and software to their normal operating state. The preoperation calculations can be to calculate variables for stepper motor control and electromagnetic stimulation control (see FIG. 5).

The coil or coils are moved at a step 503. In some embodiments, the coils can move at fairly high speeds (e.g., more than one revolution per second) so it may take some time to spin the coils up to the desired operational speed.

Once operational speed is attained, a determination is made whether current should be applied at a step 505. At some locations of the coils, it may be desirable not to apply current in order to prevent areas from being exposed to electromagnetic radiation. If existent, these areas would be identified and protected when the electromagnetic stimulation control information is calculated (see FIG. 5).

Otherwise, current is applied to the coils at the current location at a step 507. The current acts to direct electromagnetic energy at the target. The energy and temporal aspects, can be the frequency of current pulses of the current that is applied can vary depending on the location. For example, some locations can have higher current applied than others, which is an example of an energy aspect. Additionally, the duration of the application of current can be a temporal aspect.

In some embodiments, the variables relating to the application of energy are calculated before the procedure is begun (e.g., at step 501). However, in other embodiments, the variables can also be altered during the procedure as desirable. For example, monitored data from an EKG can warrant a modification of operational variables. Other aspects and characteristics will be described in more detail in reference to FIG. 8. In practice, the rate of rotation of the electromagnet coils may be stable in a preferred embodiment through a usage of the device. This means that a rotation rate must be used that will permit appropriate magnetic pulses to be generated in accordance with the instantaneous position of the coils.

At a step 509, it is determined if the procedure is complete. If not, flow returns to step 503 and the coils are moved to the next location.

Figure 8:
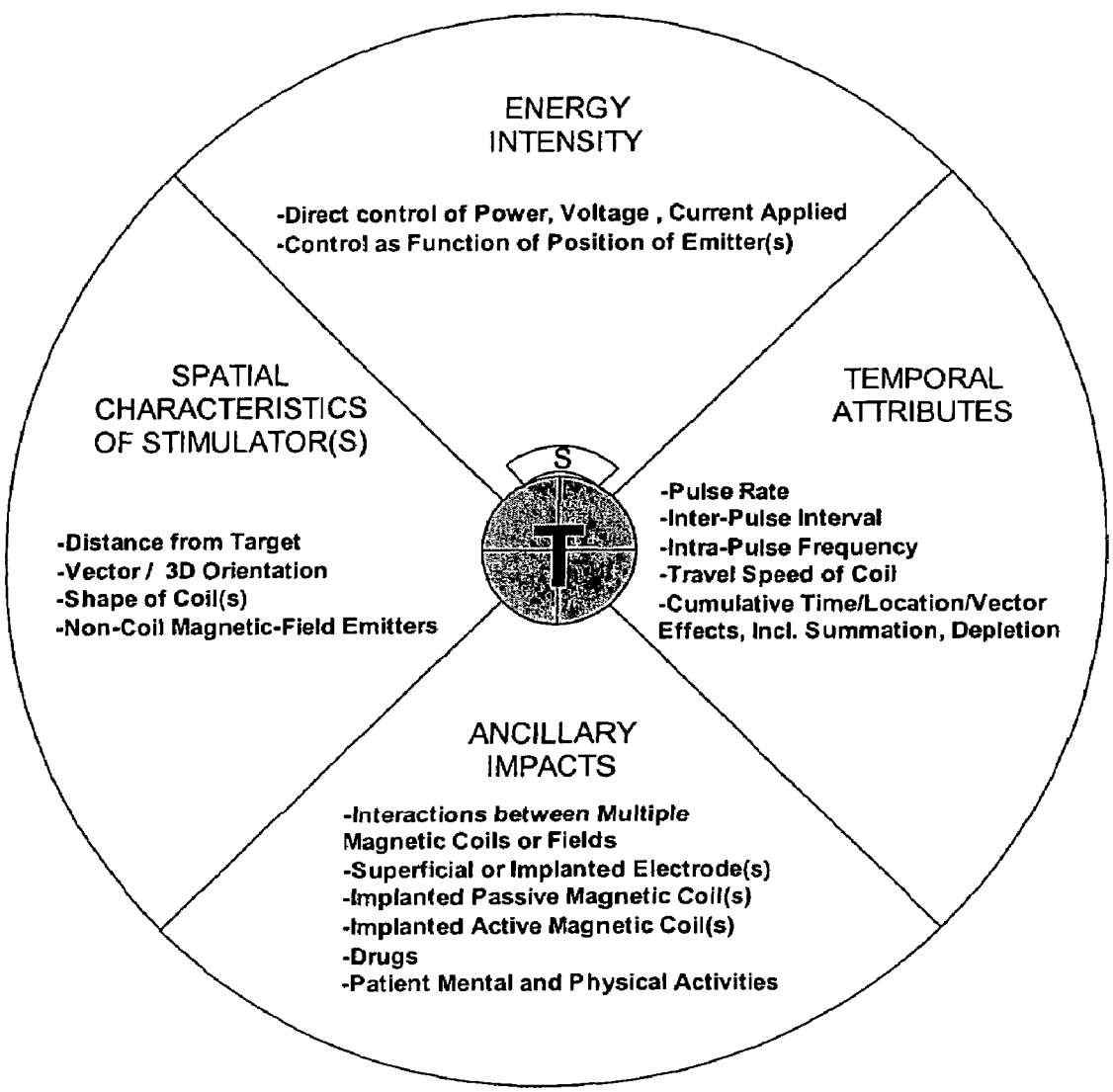
FIG. 8 illustrates various parameters that may vary the nature of the magnetic field.

FIG. 8 illustrates various parameters that may vary the nature of the magnetic field surrounding any given piece of anatomy. These characteristics can be modified in real-time as the apparatus is operating. Thus, any one or combination of multiple of these characteristics can be varied during operation.

Other than the Ancillary Impacts shown in FIGS. 7 and 9, the factors may be modified automatically by the software control system of the present invention. Typically these parameters are modified in real time as a function of the position of the emitter(s) with respect to the target, and the characteristics of the interposed tissue. One specific embodiment of automated, real time magnetic field parameter manipulation (field strength) is further described in the discussion of FIG. 9.

FIG. 9 illustrates one method of adjusting the energy applied to a magnetic coil as a function of its position in orbit, and hence its location with respect to the target. In this embodiment, variation of the magnetic field emitted is actively regulated by as a function of the relative distance between the emitter and the target, such that the distance is compensated for, and the magnetic field applied to the target remains constant at all times through the movement of the emitter. When close to a "critical structure" which should not be targeted, no pulse is emitted.

In one embodiment, this is accomplished by having the software that controls the present invention maintain a computation of the distance between each coil and the target. The inverse of the square of the distance figure is then calculated, and this number controls is used to calculate a direction, and number of "steps" for a stepper motor turn. The shaft of the step motor is, in turn, rigidly coupled to the shaft of a high-capacity rotational potentiometer interposed between TMS generator 300 and coils 6 and 10. Consequently, as one of the coils moves further from the target, the high-capacity potentiometer is automatically turned by the step motor, and the resistance is appropriately lessened so as to increase the current traveling to the coil. Conversely, as the coil in its orbit moves closer to the target, the step motor automatically dials up the resistance in the high-capacity potentiometer, thus reducing power to the coils at that time and place. In a similar manner, when the coil moves within a predetermined distance of a critical structure, a pulse of lesser energy, or no pulse at all, is emitted.

Alternatively, High Voltage Insulated Gate Bipolar Transistors (HVIGBTs) may be used in place of a potentiometer for allowing varying amounts of current across a given path.

In an alternative embodiment, current may be shunted away from the coils to a variable degree that reflects distance between coil and target. In such an embodiment, one may direct the excess current to a secondary "reserve" capacitor, which may, in turn, serve to help recharge the primary capacitors. The variable shunting can be accomplished with a parallel array of High Voltage Insulated Gate Bipolar Transistors (HVIGBTs), such as model CM1200HC-66H transistors (Powerex Inc., Youngwood Pa.), or comparable units by Mitsubishi Electric and Electronics, USA, Semiconductor Division (Santa Clara, Calif.). The units may be switched in parallel, so for a given situation when can use as many parallel components as is necessary to accommodate the electrical-current requirements For use of the CM1200HC-66H within the context of the present invention, five to six transistors in parallel may be used. One controls the modules by supplying gate-on pulses of the desired width, with minimum time-on of 5 microseconds. The surrounding circuitry may be set up vary the time period that energy is delivered to the electromagnet, and hence change the pulse parameters of the energy, or reduce overall current flow, but may also be used to control the flow of current through a resistance to a "secondary" or "reserve" capacitor to which energy is being diverted.

In still another alternative embodiment, the TMS generator unit may have several banks of different sized capacitors. In a manner analogous to a piano, in which a hammer and string await being signaled before sounding its particular note, capacitors that release different amounts of current may be relay-switched "on" at different positions within a magnet's orbit or other movement, in accordance with distance from target, under the direction of a device controller as previously described. Switching between these banks my be accomplished with device controller triggering of HVIGBTs as described above.

In a similar manner, the position of the coil can be altered to direct electromagnetic radiation at target T. Stepper motors as described above can "aim" the coil to direct electromagnetic radiation to target T. Thus, the coils may have both a rotational movement accompanied by multiple aces of movement, such as roll, pitch, yaw, up/down, and variance of the orbit itself. As should be appreciated, there are numerous other characteristics that can be modified in real-time.

Of course, several other strategies may be used for automatically modulating various parameters for the magnetic field during the processes carried out by the invention, as previously outlined in the description of FIG. 8.

Figure 10:
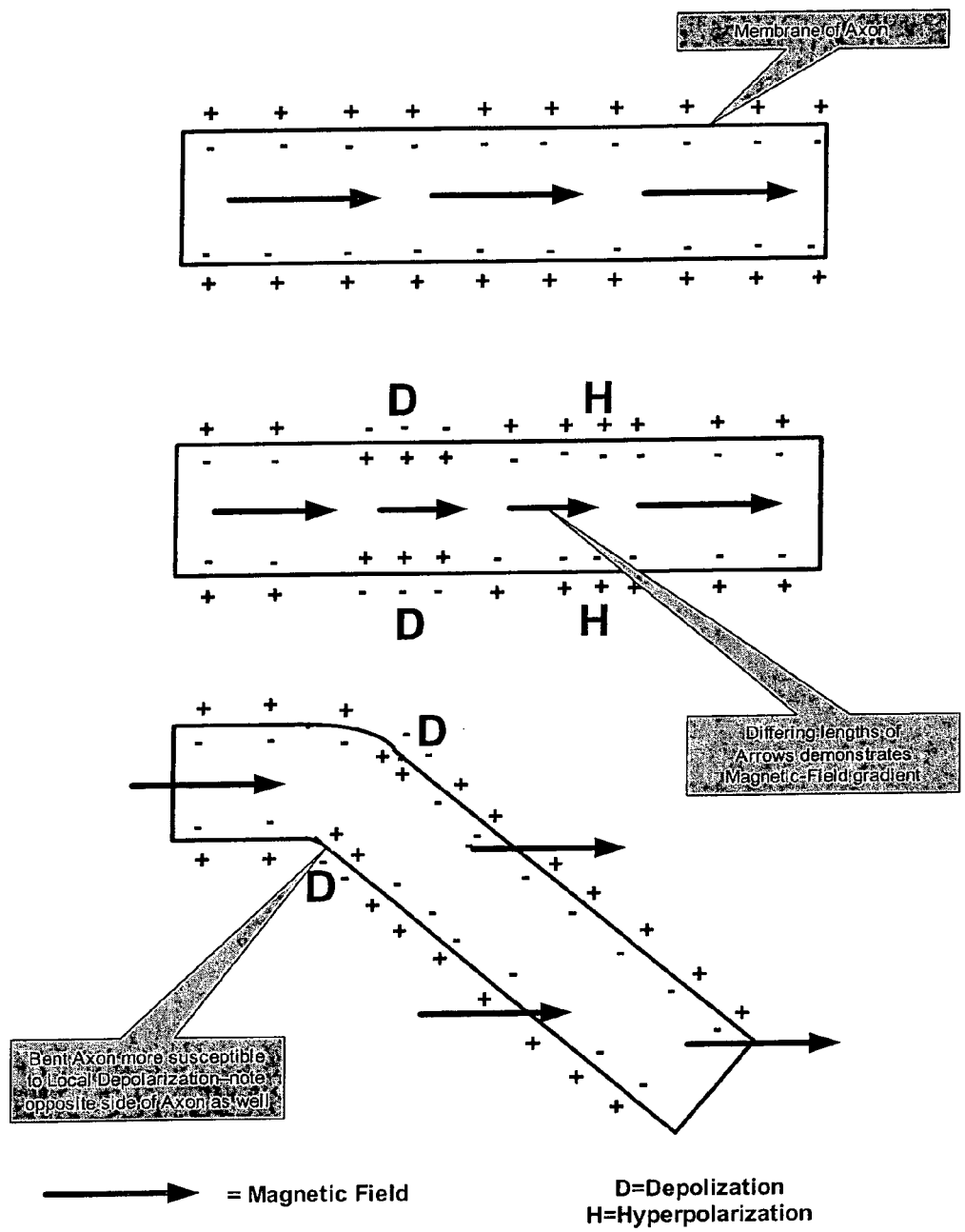
FIG. 10 illustrates mechanisms by which magnetic fields may cause depolarization of neurons.

FIG. 10 illustrates mechanisms by which magnetic fields may cause depolarization of neurons. Stimulation is most effective when the direction of the magnetic field is in the same direction of the given nerve fiber, as long as there is a magnetic-field gradient. FIG. 10 shows electromagnetic effects on some axon configurations. At rest, the outside of the membrane of the nerve axon is electrically positive with respect to the interior. As shown in the top example, even if a magnetic field (shown by the heavy arrows) that is static (indicated by the arrows being of equal length) is applied, there is no depolarization of the axon and thus no nerve conduction.

However, as shown in the middle example, if there is a field gradient (indicated by the heavy arrows representing the magnetic field being of unequal length), depolarization (or at least a change in the resting potential) of the nerve membrane can occur. In such situations, hyper-polarization can occur as well. As shown in the lower example, at the location of a bend in an axon, depolarization of the membrane can occur even in the presence of a static electromagnetic field. Note that the heavy arrows are of equal length like those in the top example. The gradient of magnetic field along a straight axon and the lack of the requirement for a gradient across a bent axon work because in both cases there exists a spatial derivative of the field. Additionally, the movement of the coil in and of itself results in movement of the magnetic field and thereby may contribute to depolarization or hyperpolarization of neurons.

A sensor-laden phantom, or effigy of a human head, may be used to study the effects of the TMS device and to modify or otherwise optimize parameters. Neural modeling may play an important role in the functionality of the phantom, and in the planning for a specific procedure with the invention. Stimulation of nerve cells, say within the cerebral cortex or one of the nuclei or other regions in the brain, is not generally at the level of the individual neuron. Instead it is at the level of axon bundles. Further not all locations along such axon bundles are equally susceptible to electromagnetic stimulation. The points along the bundles that have the lowest threshold for excitation are where the bundles bend. Bundles may range in size from a few axons to several millimeters in size. Examples of nuclei and other brain regions are the nucleus accumbens, the amygdala, and Broca's area. Bundles of neurons connecting such areas may be activated using TMS.

One aspect of repetitive stimulation and resultant discharge of the neurons is the ability to produce long-term effects. For example, repetitive TMS stimulation at low frequencies can result medium-term neuronal depression while high-frequency excitation can result in medium-term potentiation. Medium term in this context means hours. Note that these longer term effects in which the delivery of TMS and its decoupled-in-time nervous system impacts allow creation of so-called "virtual patients" in which say disruption of speech can be temporarily induced in a person who otherwise has normal speech. Of course, the same impact can be obtained while active TMS stimulation is in process. Improvements in performance (say in solving geometric puzzles when TMS is applied to the prefrontal cortex) have also been demonstrated.

When multiple electromagnets are present, it is possibly to displace the stimulation both in terms of location and in time to permit selective activation of the target(s). Observing the functional results of stimulation of a computed or phantom-based neural model allows calibration of location for the targeted tissue of the actual patient or subject.

Figure 11:
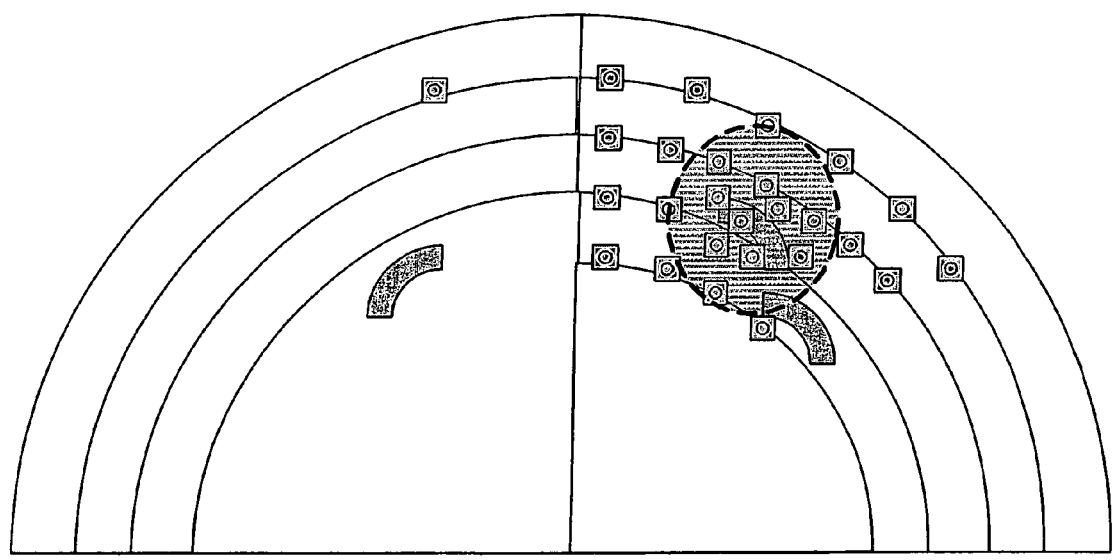
FIG. 11 illustrates aspects of the testing and treatment planning phantom model.
Figure 11:
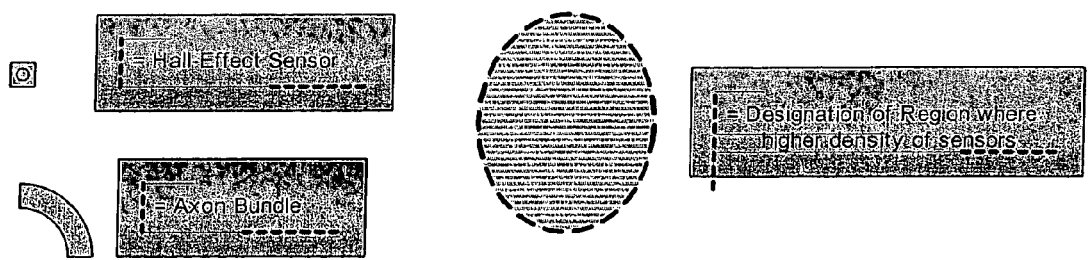

FIG. 11 illustrates aspects of the testing and treatment planning phantom model. For testing and treatment planning purposes, it is beneficial to have a physical device with which to measure the effects the electromagnetic stimulation. A phantom can represent the structure of the brain within the head, the spinal cord, the heart within the thorax, peripheral nerves within the limbs, or other suitable structure. A phantom does not just to be a representation of a human; it could easily be a representation of an animal, say one used in animal research.

One purpose of phantoms can be used to validate the predictions of simulation models prior to in vivo applications of TMS. Phantoms are useful in regard to Transcranial Magnetic Stimulation of any type (say single pulse versus repetitive TMS).

The basic form of a phantom is a three-dimensional (in alternative embodiments two-dimensional) structure in which magnetic sensors are affixed at predesignated spatial intervals, depending upon the granularity with which one desires to make measurements. A shell, composed of material such as a clear plastic, may enclose the sensors. One embodiment involves the use of Hall-effect sensors, for example, Sentron 2D-VH-11 sensors (Sentron AG, Zug Switzerland). Such sensors may make measurements in two dimensions or three dimensions. These can be arranged in alternative ways. For examples, they may be laid out on concentric shells or at the corners of virtual or real cubes. In terms of noting locations, the former may be viewed in terms of polar coordinates and the latter in Cartesian coordinates. Combinations may be included. A neuronal bundle may be represented in one way while areas peripheral to a target may be represented in another. Sensors can be thus be configured as neural bundle analogs.

FIG. 11 illustrates the use of multiple concentric shells in the fabrication of the phantom. As demonstrated, structural elements such as bent axons can be incorporated in the phantom. As indicated here, some embodiments may include a higher density of magnetic-field sensors in the region of such elements.

Figure 12A:
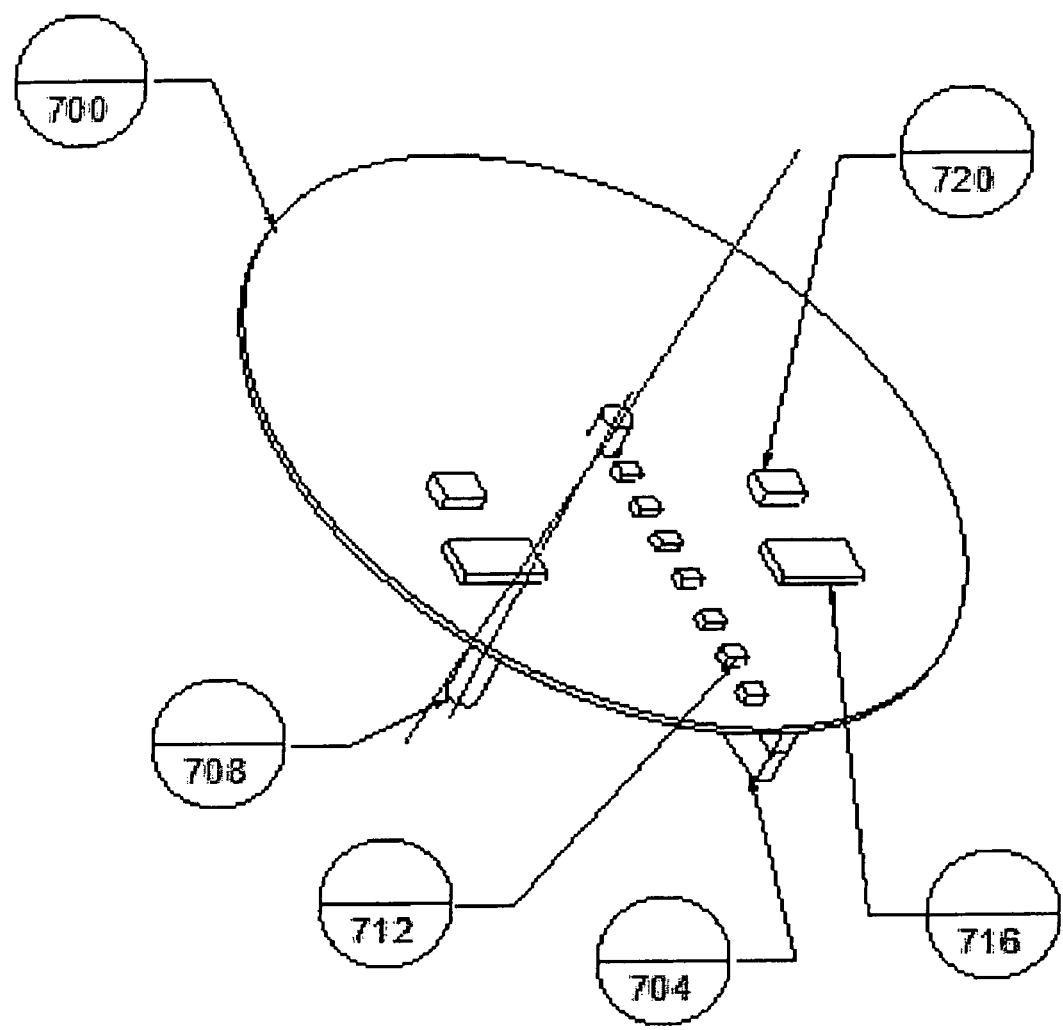
FIGS. 12A-12D show various views of another embodiment of a testing and treatment phantom model.
Figure 12B:
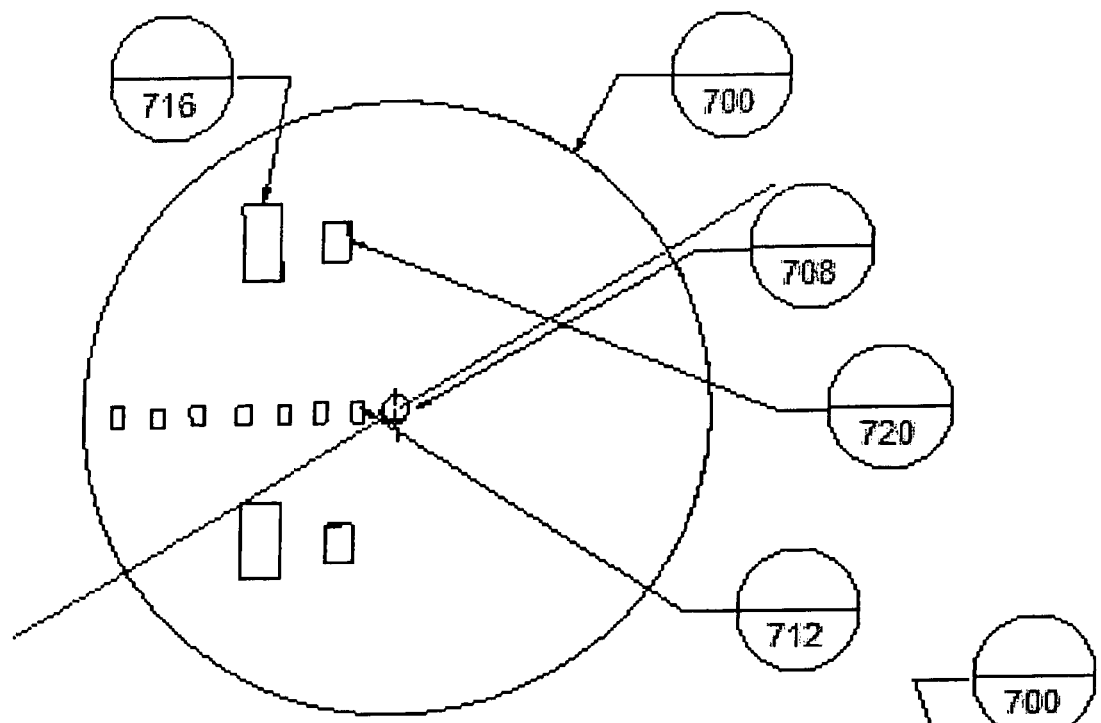
Figure 12C:
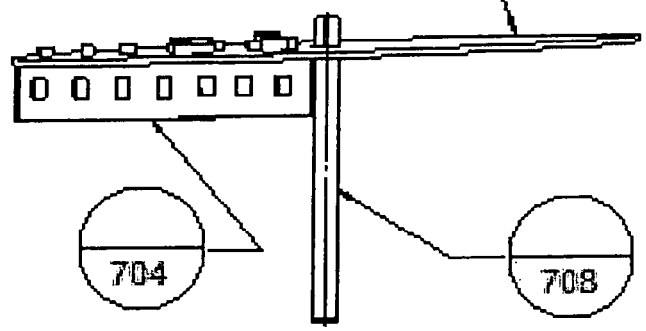

In one embodiment, the phantom sensor array is constructed to be as large in all dimensions as is the largest human brain. The sensors used should have sufficient uniformity and precision so as to enable accurate interpolation of magnetic field values in between their physical locations Another embodiment of a phantom mapping the magnetic fields present within a volume is shown in FIGS. 12A-12D. FIG. 12A shows an oblique view of the assembly, FIG. 12B the top view and FIG. 12C the side view. The phantom is comprised of a combination of a spinning disk 700 on which magnetic sensors and associated circuitry with an attached vertical-board assembly 704 with its magnetic sensors where those two boards go up and down together along threaded (worm) shaft 708. The vertical-board assembly 704 is comprised of a circuit board and the sensors 712 mounted on it.

Figure 12D:
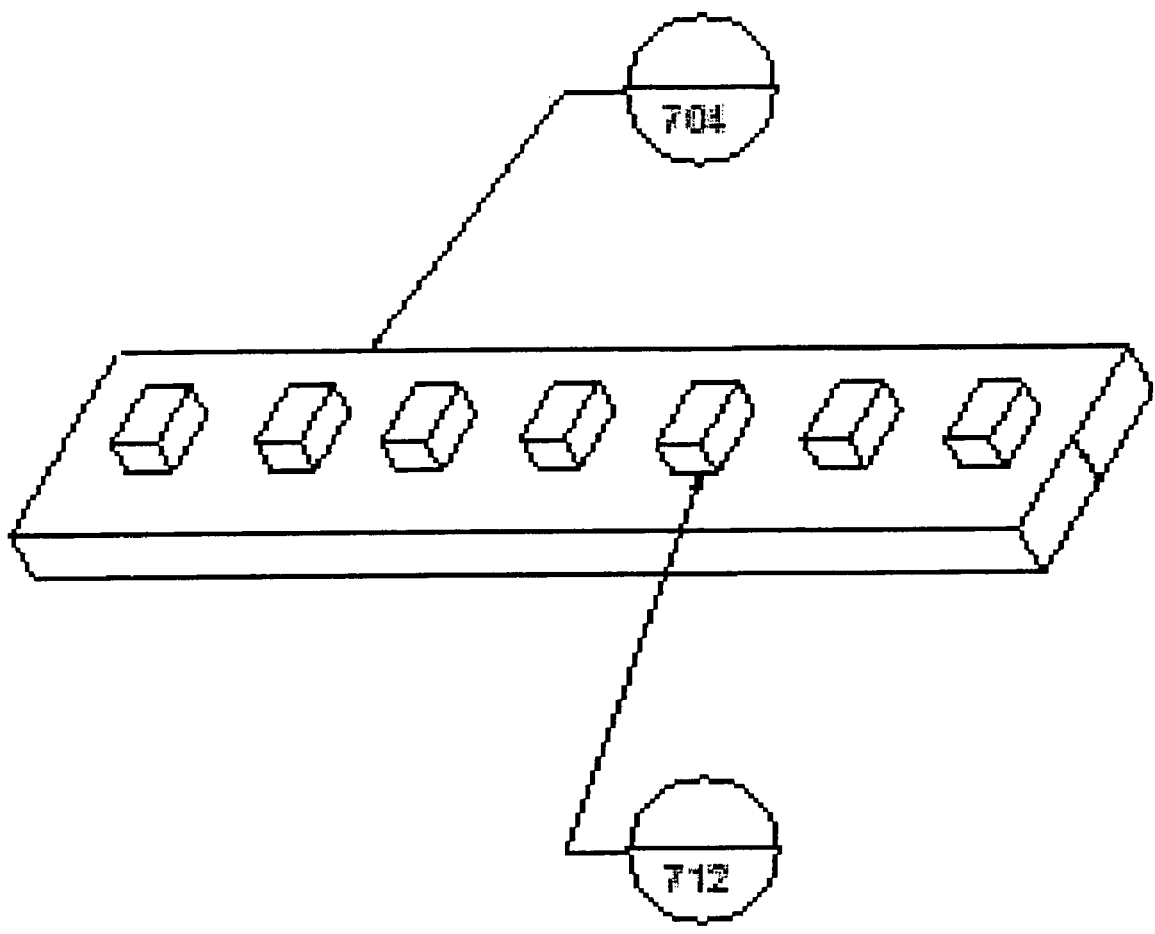

FIG. 12D shows the oblique view of the vertical-board assembly. The stepper motor that would reside at the base of that shaft with its associated control mechanism (not shown). The stepper motor would be driven by a combination of a controller board (e.g., the FET -3 from StepperWorld like 250 in FIG. 3) and an associated control/display computer.

As to the drive and associated control of threaded (worm) shaft 708, the disk 700 spins and is driven upward when the threaded shaft 708 is turned in one direction and driven downward when that shaft 708 is turned in the opposite direction. Because the rotation is back and forth rather than continuing is a single direction of rotation, no slip ring is required for the signal and power wire connections.

Alternatively, a slip ring could be employed as a cap at the top of worm gear extended through the disk 700 and held in the a constant position relative to disk 700 by riding up and down on a smooth rod that penetrates disk 700 and is held in a position perpendicular to the disk 700 by a fixture. An alternative embodiment would have the power provided by on-board batteries and bi-directional communications accomplished through RF communications.

In one embodiment, the motor is a unipolar stepping motor (e.g., Vexta PK244-01AA, Oriental Motor Co., Ltd., Tokyo, Japan; U.S. Headquarters in Torrance, Calif.) with each rotational step being 1.8 degrees. The magnetic-field intensity is measured by Hall-effect ratiometric sensors 712 that have built-in amplification (e.g., Sentron 2SA-10 from Sentron AG in Switzerland, available through GMW Associates in Santa Clara, Calif.). The 2SA-10 sensors measure low-field intensities (linear to 40 milliTeslas).

For array positions where high-field intensities are required, a Hall-effect sensor with a larger range is used. An example is the Sentron 2D-VH-11 which can measure up to 2 Teslas. Use of the Sentron 2D-VH-11 requires separate amplifiers. In this embodiment, the sensors measure the magnetic-field intensity along both the X and Y axes. The outputs of the Hall-effect sensors go to an analog multiplexer 716 controlled by microcontroller 720 which also performs the analog-to-digital conversion on the analog signal output by analog multiplexer 716.

The digital-control signals output by the microcontroller 720 determine which one of the analog signals going into the analog multiplexer 716 is routed to its analog output at any point in time. The magnetic-field intensity along the Z axis is measured by the sensors 712 on vertical-board assembly 704 that have their outputs routed to the analog multiplexers 716 on disk 700 with control and analog-to-digital conversion provided microcontrollers 720. If 2D sensors are used, only one of the two channels would normally be employed.

In an alternative embodiment, the output of the multiplexers could be run into, the multiplexers controlled by a USB-mediated data-acquisition device such as the Measurement Computing Corp. (Middleboro, Mass.) PMD-1280LS that provides (among other functions) analog-to-digital and digital-signal outputs. The latter are used to control the multiplexers.

Figure 12E:
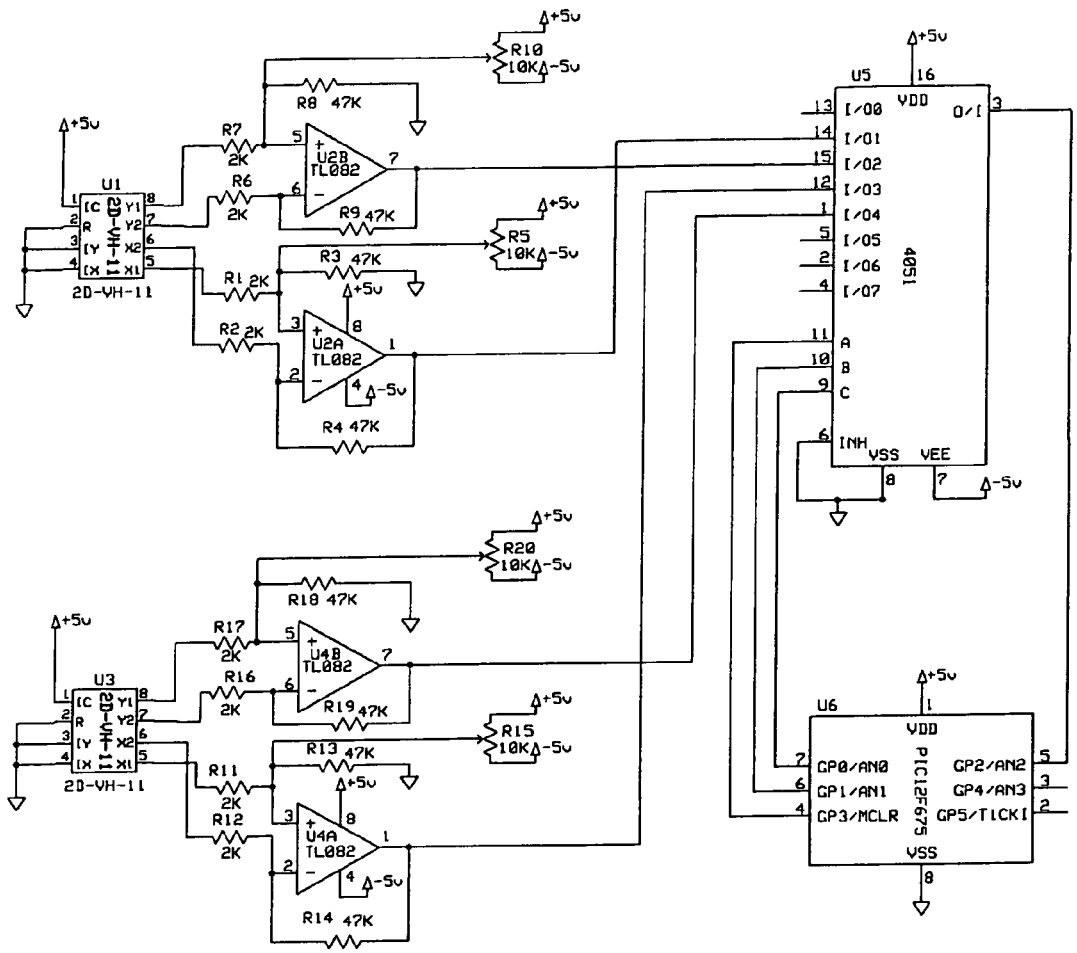
FIG. 12E shows electronics of the type that can be utilized to support the physical embodiment of FIGS. 12A-12D.

A detailed embodiment of the electronics of the type needed to support the physical embodiment of FIGS. 12A-12D is shown in FIG. 12E. As previously noted, a difference is that in FIG. 12A, the packages containing the sensors 712 include the amplification function as well (e.g., Sentron 2SA-10 from Sentron) as the Hall-effect magnetic-field-intensity sensing. In the schematic diagram shown in FIG. 12E, the Hall-effect sensors (Sentron 2D-VH-11 that can measure up to 2 Tesla intensities) U1 and U3 are separate from the amplification functions provided by operational amplifiers U2A/U2B and U4A/U4B in TL082 (e.g., from Texas Instruments).

In the circuit in FIG. 12E, the 2D-VH-11 sensor, say U1, can measure the magnetic-field strength in two dimensions, X and Y with differential outputs on pins 5/6 and 7/8 respectively. These differential outputs go through input resistors R1 and R2 for the X-axis pair where because of the ratio of the feedback resistor R3 (47K ohm) to the input resistors R1 and R2 (each 2K ohms), the amplification is approximately 24. Note, capacitors could also be included, but are not shown here. The TL082 contains 2 operational amplifiers in one package, so the description of what happens is the same for both.

The potentiometer R5 (10K ohms) is used to balance the differential inputs coming in through R1 and R2 for zero input. For a single sensor, the signal path for each of the X and Y dimensions goes through a stage of amplification (say U2A and U2B of the TL082 respectively) and the analog outputs go on to an analog multiplexer 4051 (e.g., from Philips Electronics) U5 (pin 14 for the output of operational amplifier U2A) whose control is provided by microcontroller U6 (PIC 12F675 from Microchip Technology, Chandler, Ariz.) via digital outputs on U6, pins 4, 6, and 7 to U5 inputs 9, 10, and 11 respectively. The analog output of U5 (pin 3) also goes into analog-to-digital converter on microcontroller U6 (pin 5). Communication of the digital result to a computer for further processing and display would occur via serial communications using say pin 3 on U6.

The embodiment shown in FIG. 12E shows only two 2-D Hall-effect sensors, but the number could be similarly expanded as is well known in the art. Depending on the total number of such sensors, not only would the number of associated operational amplifiers need to multiplied, the number of analog multiplexers 4051 might need to be multiplied as well, and either the number of microcontrollers increased or a microcontroller with increased number of digital output channels utilized.

All of the Hall-effect sensors within an array need not all be capable of measuring the same ranges of values. In addition, while 2-dimensional Hall-effect sensors have been utilized in the described embodiments, an alternative embodiment could employ 3-dimensional Hall-effect sensors.

Figure 12F:
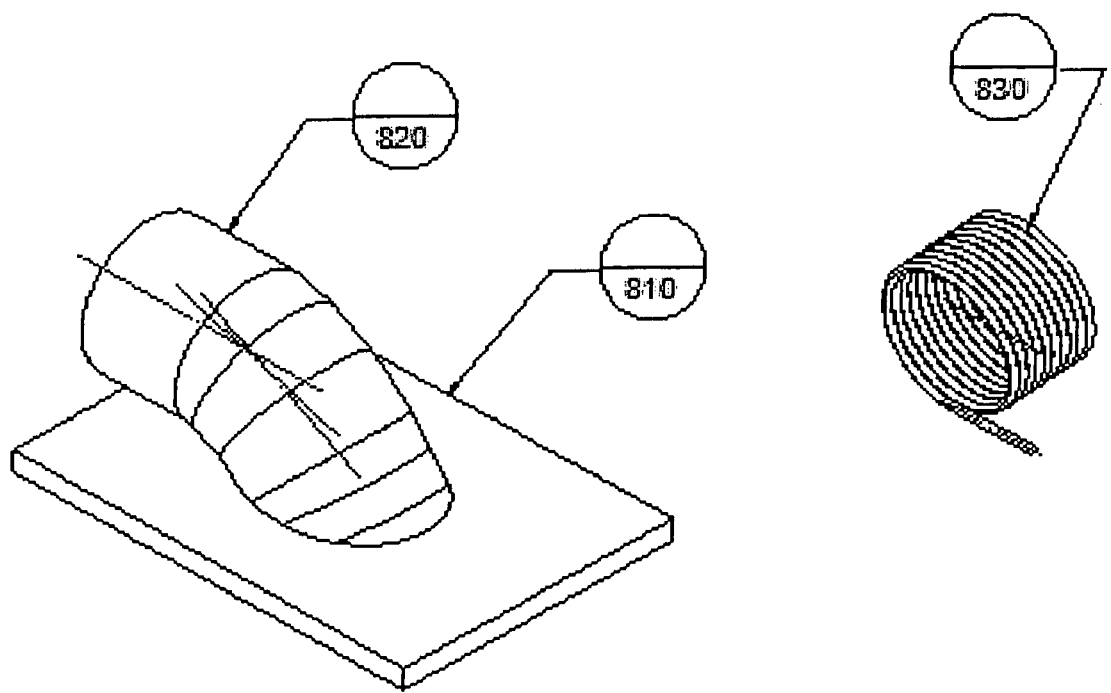
FIG. 12F shows a representation an axon bundle, such as a bent axon, that can be utilized in embodiments of the invention.

Another aspect of phantom embodiments is that of a representation an axon bundle, preferably a bent axon as shown in FIG. 12F. The active-element container 820 is mounted on board 810. The current-measuring elements incorporated within the active-element container 820 are coils of the type 830. The number and orientations of the coils 830 are determined by the location and orientation of the active-element container 820 which is in turn determined by the situation being modeled.

Each of the coils 830 is to be terminated by a high-value precision resister with the voltage measured across the resistor proportional to the current generated by the magnetic field generated by the TMS apparatus. By applying Ohm's law, the amount of current so induced can be calculated. The appropriately shaped axon-bundle representation can be placed within the phantom in the location within the volume where it would anatomically occur. Thus, physical structures in the phantom can be designed to represent and measure electromagnetic energy that would be applied to physical structures within the object (e.g., a patient).

Figure 13:
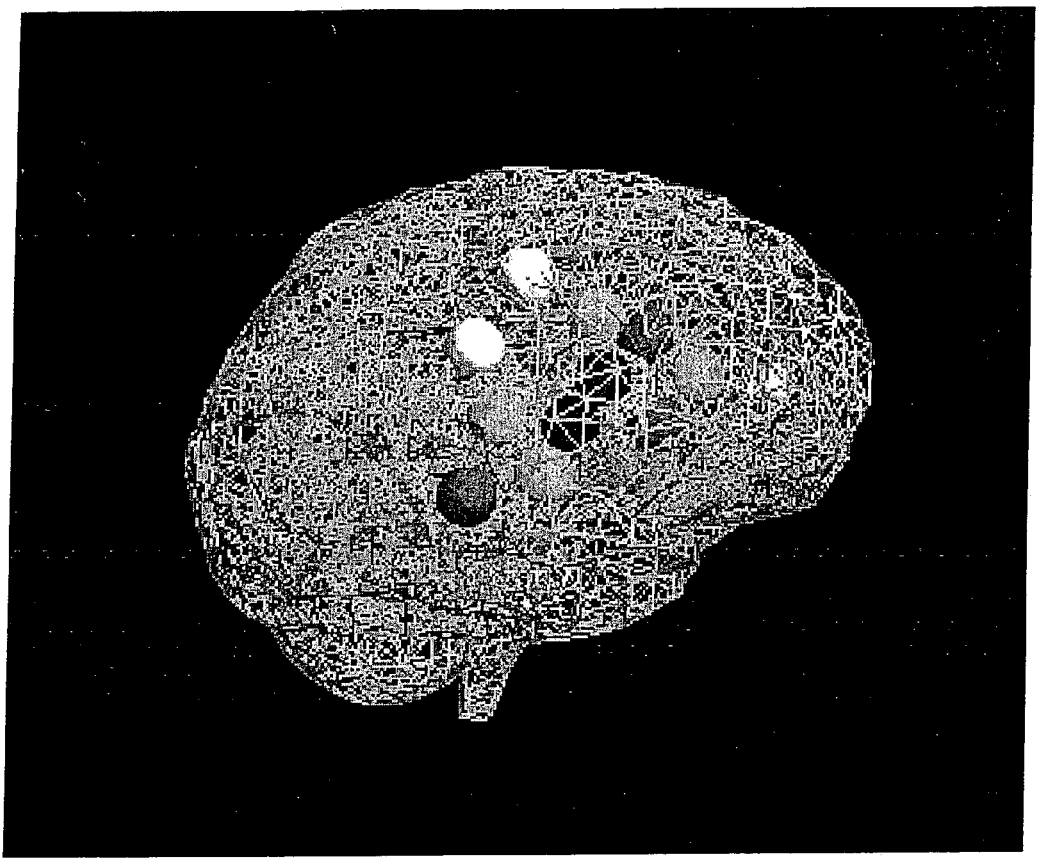
FIG. 13 shows a computerized graphical interface of the planning and testing phantom during use.

Additionally, in a physical representation (as opposed to display on a computer screen as shown in FIG. 13), tri-color LEDs (e.g., Model RL5-RGB-C from Red Line, Inc., St. Louis, Mo.) can be used to display the relative magnetic intensity throughout a volume or on a single plane. Say, for example, the three colors were red, green, and blue. If there were no field at a given point, the given LED would not be lit up. If a low-intensity magnetic field were present, the blue light would be illuminated, for a medium-intensity magnetic field, the green light would be illuminated, and for a high-intensity magnetic field, the red light would be illuminated. If the tri-color LED supports colors being turned on simultaneously, then more magnetic-intensity levels could be indicated. Note that in an alternative embodiment, clusters of single-color LEDs could be alternatively used.

A graphic display system, such as that illustrated in FIG. 13, shows the values of the magnetic field as seen and as interpolated throughout the grid, and represented, for example, as colored spheres within a representation of 3D space of the brain. The colors of the spheres might change from a cool blue to yellow, and then to red as the magnetic field at those points crosses certain pre-designated thresholds. This display may related to the intensity of the magnetic field at any given instant, or possibly more useful, the magnetic field at each point as integrated over a pre-designated period of time.

Next, a medical image, preferably a 3D volumetric image such as an MRI scan, of each specific patient is obtained. A translucent volume rendering of that 3D MRI image matrix is then merged with the graphic display of the magnetic field in 3-D space described above. In this way, the exact location of a targeted anatomical structure can be stimulated in simulation before that actual patient is subjected to a certain pre-planned sTMS treatment. Accordingly, 2D slices may also be used to represent subsets of the same composite data. In the case of a series of 2D composites, there is no need for translucency.

FIG. 13 is a color plate of a computerized graphical interface of the planning and testing phantom during use. A 3-dimensional wire frame of a human brain is displayed. Within the wire frame, as well as on its surface, and specific locations are spheres that represent the state of magnetic field sensor elements within the phantom. These spheres are designed to change their visible characteristics as a function of the stimulation that they are receiving.

For example, in this figure, the spheres are set to be entirely transparent and invisible if no magnetic field above a pre-designated threshold is detected at that location. As that threshold is exceeded, the spheres are rendered as white. Those sensors detecting yet higher levels of magnetic field have their corresponding graphical spheres shaded as blue, yellow, and orange, up to a highest level at which they are shaded red. At the higher colored levels of the display, depolarization of a corresponding actual neuron or nerve bundle is suggested.

In other embodiments, the thresholds for various locations or areas of the object are compared against the electromagnetic energy that is measured at those locations. Thus, the display can indicate whether the desired threshold or thresholds have been crossed at target locations of interest, where each threshold can be associated with the target location.

In an alternative embodiment, a translucent volumetric rendering of a brain, or part of a brain, or other intra-orbital volume my replace the wire frame shown in this figure.

This graphical display may be set to display information about the magnetic field sensors in a variety of ways. For example, they may reflect the precise strength of magnetic field detected at that particular instant. Alternatively, they my be set to display the strength of the magnetic field at that point as mathematically integrated over a designated period of time. In this latter mode of operation, the display more accurately models the behavior of actual neurons, whose depolarization behavior results from a summation process that occurs over a finite period of time on the neuronal membrane, in competition with an ongoing re-polarization effort by each nerve cell. By including re-polarization rate factors in the equation, interactive models of neuronal fatigue, depletion, and inhibition are also obtained.

This same graphical interface may also be used in a full computer-simulation mode without connection to a physical phantom, or use of an actual TMS device. In that mode of operation, magnetic fields are calculated based on known characteristics of the emitter device, including magnetic field parameters, and location of the source at any given moment in time.

The invention described herein has a great number of neuroscience research and clinical psychiatric, neurological, and neurosurgical applications. Use of this invention may benefit patients suffering from a numerous different medical conditions, a few of which follow. For example Parkinson's disease patients might experience a decrease in tremor and rigidity during stimulation of subthalamic nuclei and globus pallidus interna (as occurs following neurosurgical electrode implantation). Similarly the invention may be used to locate the optimal site for deep brain stimulating electrode by non-invasively testing the effect of brain stimulation at several different candidate regions. Chronic pain patients might experience a decrease in pain during stimulation of the septum (as seen in the experimental implantation of electrodes in laboratory animals), or by stimulation-induced fatigue or depletion of the anterior cingulate gyrus. Obsessive-Compulsive Disorder patients might experience a decrease in symptoms during stimulation to the anterior limb of the internal capsule, or of subthalamic nuclei (as documented following electrode implantation). Alzheimer's Disease patients might experience an improved ability to transfer short-term memory into long-term memory during stimulation to hippocampal structures such as the dentate gyrus, CA1, and CA3 fields. The current invention is readily adapted for Magnetic Seizure Therapy and could make the process more accurate and efficient.

A version of TMS (so-called supercharged version) is MST (Magnetic Seizure Therapy) used to generate seizures in anesthetized patients for the treatment of depression. Focusing the stimulation that elicits such seizures offers the opportunity to prevent the spread of the seizure to adjacent areas and thus avoid side effects due to the passage of electric current through the brain occurs in electroconvulsive therapy (ECT).

While the above is a complete description of preferred embodiments of the invention, various alternatives, modifications, and equivalents can be used. It should be evident that the invention is equally applicable by making appropriate modifications to the embodiments described. Therefore, the above description should be taken as limiting the scope of the invention that is defined by the metes and bounds of the appended claims along with their full scope of equivalents.

What is claimed is:

1. A method of applying electromagnetic energy to a target, comprising:
    moving a coil relative to the target; and
    applying current to the coil from a plurality of locations to direct magnetic fields to the target and magnetically stimulate the target, wherein the current is applied to the coil at a sufficiently rapid frequency prevent re-polarization of the target as the coil is moved, such that the magnetic stimulation of the target is higher at the target than at a region interposed between the target and the coil.

2. The method of claim 1, further comprising adjusting the current to the coil at each location so that the magnetic field at the target is constant.

3. The method of claim 2, wherein the current is adjusted by the inverse of the square of the distance between the coil and the target.

4. The method of claim 1, further comprising selectively not applying current to the coil at a location where directing a magnetic field at the target would expose an area interposed between the target and the coil to undesirable magnetic field energy.

5. The method of claim 1, further comprising selecting a duration for applying the current depending on a location of the coil.

6. The method of claim 1, further comprising selecting an inter-pulse interval for applying the current depending on a location of the coil.

7. The method of claim 1, further comprising selecting an intra-pulse frequency for applying the current depending on a location of the coil.

8. The method of claim 1, further comprising selecting a speed of movement of the coil.

9. The method of claim 1, further comprising a plurality of coils.

10. The method of claim 1, wherein the coil is a transcranial magnetic stimulation (TMS) coil.

11. The method of claim 1, further comprising the step of aiming the coil at the target, wherein the target is a sub-cortical brain region.

12. A method of applying electromagnetic energy to a target, comprising:
    magnetically stimulating a neuronal target from a first location by applying current to a coil;
    moving the to a second location relative to the target;
    continuing the magnetic stimulation of the neuronal target from the second location by applying current to the coil, wherein the magnetic stimulation is greater at the target than the magnetic stimulation at a region interposed between the target at the coil;
    wherein the current applied to the coil at the first and second locations is applied at a frequency sufficient to prevent re-polarization of the target as the coil is moved.

13. The method of claim 12, further comprising adjusting the current to the coil at each location so that the magnetic field at the target is constant.

14. The method of claim 13, wherein the current is adjusted by the inverse of the square of the distance between the coil and the target.

15. The method of claim 12, further comprising selectively not applying current to the coil at a location where directing a magnetic field at the target would expose an area interposed between the target and the coil to undesirable magnetic field energy.

16. The method of claim 12, further comprising selecting a duration for applying the current depending on a location of the coil.

17. The method of claim 12, further comprising selecting an inter-pulse interval for applying the current depending on a location of the coil.

18. The method of claim 12, further comprising selecting an intra-pulse frequency for applying the current depending on a location of the coil.

19. The method of claim 12, further comprising selecting a speed of movement of the coil.

20. The method of claim 12, further comprising a plurality of coils.

21. The method of claim 12, wherein the coil is a transcranial magnetic stimulation (TMS) coil.

22. The method of claim 12, further comprising the step of aiming the coil at the target, wherein the target is a sub-cortical brain region.

23. A method of applying electromagnetic energy to a target brain region, comprising:
    magnetically stimulating a target brain region by applying current to a coil from a first location;
    moving coil relative to the target brain region; and
    continuing to magnetically stimulate the target brain region by applying current to the coil when the coil is at a second location to direct magnetic fields to the target brain region, wherein the magnetic stimulation is applied at a frequency sufficient to prevent re-polarization of the target brain region as the coil is moved, such that the magnetic stimulation over time at the target brain region sums and is higher at the target brain region than at brain regions interposed between the target brain region and the coil.

24. The method of claim 23, wherein the step of magnetically stimulating a brain region comprises magnetically stimulating a deep brain region.

25. The method of claim 24, wherein the step of magnetically stimulating a deep brain region comprises magnetically stimulating a sub-cortical brain region.

* * * * *